(12) United States Patent
Ulrich et al.

(10) Patent No.: US 6,689,777 B2
(45) Date of Patent: Feb. 10, 2004

(54) ANTI-MALARIAL COMPOUNDS, COMPOSITIONS AND METHODS

(75) Inventors: Peter C. Ulrich, Portland, OR (US); Anthony Cerami, Croton-on-Hudson, NY (US)

(73) Assignee: Kenneth S. Warren Institute, Ossining, NY (US)

( * ) Notice: Subject to any disclaimer, the term of this patent is extended or adjusted under 35 U.S.C. 154(b) by 0 days.

(21) Appl. No.: 10/278,729

(22) Filed: Oct. 23, 2002

(65) Prior Publication Data

US 2003/0186993 A1 Oct. 2, 2003

Related U.S. Application Data

(60) Provisional application No. 60/335,067, filed on Oct. 24, 2001, and provisional application No. 60/348,757, filed on Oct. 23, 2001.

(51) Int. Cl.[7] .................. C07D 277/60; A61K 31/425

(52) U.S. Cl. .................. 514/232.8; 514/252.13; 514/366; 544/133; 544/368; 548/150

(58) Field of Search .................. 548/150; 514/366, 514/252.13, 232.8; 544/133, 368

(56) References Cited

PUBLICATIONS

Ulrich et al, Journal of Medicinal Chemistry, vol. 25, No. 6, pp. 654–657, 1982.*

* cited by examiner

*Primary Examiner*—Zinna Northington Davis
(74) *Attorney, Agent, or Firm*—Frederick J. Hamble

(57) ABSTRACT

The present invention is directed to substituted naphthothiazolium, aromatic guanylhydrazones, and other compounds and compositions with anti-malarial activity useful for the treatment and prophylaxis of malaria. The compounds are provided for the treatment of malaria or the sequelae of malarial infection, for depolymerizing malaria pigment (hemozoin), and for ameliorating the adverse effects of hemozoin on host cells.

8 Claims, 1 Drawing Sheet

ANTI-MALARIAL COMPOUNDS, COMPOSITIONS AND METHODS

CROSS-REFERENCE TO RELATED APPLICATIONS

Priority under 35 U.S.C. §119(e) is claimed to Provisional Application Serial No. 60/348,757, filed Oct. 23, 2001 and Provisional Application Serial No. 60/335,067, filed Oct. 24, 2001, and which is incorporated herein by reference in its entirety.

FIELD OF THE INVENTION

The present invention is directed to substituted naphthothiazolium; aromatic guanylhydrazones, and other compounds and compositions with anti-malarial activity useful for the treatment and prophylaxis of malaria.

BACKGROUND OF THE INVENTION

Malaria continues to be a major disease in most of the developing world. The estimated 300 million cases that occur per year result in considerable morbidity (e.g. fever, malaise, anorexia, anemia) and mortality of over 2 million children under the age of five (1). The intracellular protozoa, *P. falciparum*, accounts for greater than 95% of the malaria deaths. An important contributor to the increase in the incidence of malaria over the past 30 years has been the development of resistance of the malarial parasite to quinoline-containing anti-malarials such as chloroquine and quinine (2). In addition, it has been recognized that a number of complications, such as anemia, failure to gain weight and immunosuppression, associated with malaria infections continue to occur for weeks and even months after the parasites are cleared from the body (3,4,5).

The malaria pigment, hemozoin, is a unique polymer of heme molecules produced by the malaria parasite as a product of hemoglobin catabolism within the food vacuole (6) that serves to protect the parasite from potentially toxic free heme, as well as to induce pathology in the infected host. Over time, the intraerythrocytic parasite exhausts this energy and protein supply and then begins the next stage of its life cycle. Through a series of DNA and membrane divisions, each trophozoite will form 8–12 merozoites and one large "garbage bag" containing polymerized hemozoin. When the infected red blood cell bursts, the merozoites go o to infect new cells and the hemozoin is released into the blood stream where it is scavenged by macrophages. The hemozoin is extremely stable and remains undegraded in the host organism for an extended period of time (years), mostly concentrated in the liver, kidneys and spleen.

Studies have demonstrated that hemozoin, either chemically made or isolated from the natural source, stimulates the production of tumor necrosis factor (TNF), and the macrophage inflammatory proteins, MIP-1α and MIP-1β, in both murine macrophages and in human peripheral blood monocytes in vitro. This cytokine release is specific for hemozoin and not secondary to ingestion of particulate matter (e.g., latex beads), heme-containing compounds (hematin or hemin crystals) or to contamination with endotoxin (25). Administration of chemically synthesized hemozoin to rats provoked a dysregulation of temperature comparable to that observed with the administration of endogenous pyrogens, such as TNF and MIP-1α.

In contrast to induction of cytokines by lipopolysaccharide (LPS) which peaks within hours and is promptly shut off, the indigestible hemozoin continues to induce TNF for 72 hours. This prolonged stimulation of cytokines is believed responsible for the elevated serum levels of TNF that are observed many weeks after malaria infections have been cured in children (28). The indigestible hemozoin continues to stimulate the macrophage to produce cytokines for long periods prolonging the time needed for recovery after resolution of the infection. Furthermore, macrophages laden with hemozoin have a number of impaired effector functions (7,8,9). These include decreased ability to mount an oxidative burst, decreased killing of pathogens, antigen presentation and a depression of cellular immunity.

Since plasmodia have evolved this unique mechanism to detoxify potentially toxic heme, interfering with its production would adversely effect the parasites since they have no mechanism to rid heme from the food vacuole. In contrast, mammals use heme oxygenase to break down heme to bilirubin. It has been proposed that the mechanism of action of quinoline containing drugs such as chloroquine and quinine was by interference with the heme polymerization process in the food vacuole of the parasite (26,27). This inhibition would lead to the accumulation of free heme which would be toxic to the parasite. The structure of hemozoin and the prevention of its formation by chloroquine has been confirmed by several workers (10,11,12).

It is towards the development of new antimalarial compounds which depolymerize hemozoin, both to kill parasites and reduce hemozoin toxicity in the host, that the present application is directed.

The citation of any reference herein should not be construed as an admission that such reference is available as "Prior Art" to the instant application.

SUMMARY OF THE INVENTION

In accordance with the present invention, a method is provided for treating a mammal suffering from malaria or the sequelae of malarial infection comprising administering a therapeutically effective amount of a compound of the formula:

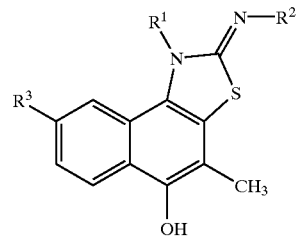

wherein $R^1$ is hydrogen, alkenyl, hydroxy(lower)alkyl, di[(lower)alkyl]amino(lower)alkyl, a heterocyclic, group, or a lower alkyl group optionally substituted by a heterocyclic group; $R^2$ is cycloalkyl, alkenyl, lower alkyl, hydroxy(lower alkyl), di[hydroxy(lower)alkyl]amino(lower)alkyl, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor. $R^1$ may be for example hydroxyethyl, allyl; dimethylaminopropyl, morpholinopropyl, or an ethyl group. $R^2$ may be for example a cyclohexyl, allyl, phenyl, morpholinopropyl, methylpiperazinopropyl, di(hydroxyethyl)aminopropyl, ethyl, propyl, hydroxyethyl, or 3-[1-(guanylhydrazono) ethyl]phenyl group. Non-limiting examples of salts include hydrochloride, dihydrochloride, sulfate, hemisulfate, and dimethanesulfonate. Preferred compounds include but are not limited to:

1-ethyl-2-(ethylimino)-1,2-dihydro-4-methylnaphtho[1,2-d]thiazol-5-ol;

1,2-dihydro-1,4-dimethyl-2-[[3-(4-methyl-1-piperazinyl)propyl]imino]naphtho[1,2-d]thiazol-5-ol;

2-(cyclohexylimino)-1,2-dihydro-4-methyl-1-[3-(dimethylamino)propyl]naphtho[1,2-d]thiazol-5-ol;

2-[[3-[1-[2-(aminoiminomethyl)hydrazono]ethyl]phenyl]amino]-4-methylnaphtho[1,2-d]thiazol-5-ol;

2-[[3-[bis(2-hydroxyethyl)amino]propyl]imino]-1,2-dihydro-1,4-dimethylnaphtho[1,2-d]thiazol-5-ol;

1,2-dihydro-4-methyl-1-(2-propenyl)-2-(2-propenylimino)naphtho[1,2-d]thiazol-5-ol;

4-methyl-2-(2-propenylamino)naphtho[1,2-d]thiazol-5-ol;

2-(cyclohexylimino)-5-hydroxy-4-methylnaphtho[1,2-d]thiazole-1(2H)-ethanol;

1,2-dihydro-2-[(2-hydroxyethyl)imino]-1,4-dimethylnaphtho[1,2-d]thiazol-5-ol;

1,2-dihydro-1,4-dimethyl-2-(phenylimino)naphtho[1,2-d]thiazol-5-ol;

1,2-dihydro-4-methyl-2-(phenylimino)naphtho[1,2-d]thiazol-5-ol;

4-methyl-2-[[3-(4-morpholino)propyl]amino]naphtho[1,2-d]thiazol-5-ol;

8-[1-[2-(aminoiminomethyl)hydrazono]ethyl]-2-(butylimino)-1,2-dihydro-1,4-dimethylnaphtho[1,2-d]thiazol-5-ol;

2-(cyclohexylimino)-1,2-dihydro-4-methyl-1-[3-(4-morpholino)propyl]naphtho[1,2-d]thiazol-5-ol;

2-(cyclohexylimino)-1,2-dihydro-4-methyl-1-[3-(4-methyl-1-piperazinyl)propyl]naphtho[1,2-d]thiazol-5-ol;

2-[[3-(dimethylamino)propyl]imino]-1,2-dihydro-1,4-dimethylnaphtho[1,2-d]thiazol-5-ol;

1,2-dihydro-4-methyl-1-[3-(dimethylamino)propyl]-2-(1-methylethyl)aminonaphtho[1,2-d]thiazol-5-ol.

The present invention is also directed to a method for treating a mammal suffering from malaria or the sequelae of malaria infection comprising administering a therapeutically effective amount of a compound of the formula:

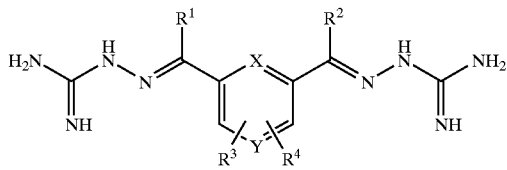

wherein X and Y are independently N or CH, with the proviso that X and Y are not both N; $R^1$ and $R^2$ are both hydrogen or lower alkyl groups; wherein $R^3$ and $R^4$ are independently hydrogen, hydroxy, amino, lower alkoxy, lower alkyl or a 1-(guanylhydrazono)alkyl group; or a pharmaceutically acceptable salt thereof. Non-limiting examples of salts include hydrochloride, dihydrochloride, sulfate, hemisulfate, and dimethanesulfonate. Preferred compounds include but are not limited to:

2,2'-[(4,6-dihydroxy-1,3-phenylene)diethylidyne]bis(hydrazinecarboximidamide);

2,2'-[(4-hydroxy-1,3-phenylene)diethylidyne]bis(hydrazinecarboximidamide);

2,2'-(1,3-phenylenediethylidyne)bis(hydrazinecarboximidamide);

2,2'[(2-hydroxy-5-methyl-1,3-phenylene)dimethylidyne]bis(hydrazinecarboximidamide);

2,2'-[(2-methoxy-5-methyl-1,3-phenylene)dimethylidyne]bis(hydrazinecarboximidamide);

2,2'-[(2-amino-1,3-phenylene)diethylidyne]bis(hydrazinecarboximidamide);

2,2'-[(4-hydroxy-1,3-phenylene)dimethylidyne]bis(hydrazinecarboximidamide);

2,2'-(1,3-phenylenedimethylidyne)bis(hydrazinecarboximidamide);

2,2'-(2,6-pyridinediyldiethylidyne)bis(hydrazinecarboximidamide);

2,2'-(3,5-pyridinediyldiethylidyne)bis(hydrazinecarboximidamide);

2,2'-[(2,6-dimethyl-3,5-pyridinediyl)diethylidyne]bis(hydrazinecarboximidamide);

2,6-bis[1-[[(dimethylamino)acetyl]hydrazono]ethyl]pyridine;

2,2'-[(5-amino-1,3-phenylene)diethylidyne]bis(hydrazinecarboximidamide);

2,2'-[(5-hydroxy-1,3-phenylene)diethylidyne]bis(hydrazinecarboximidamide);

2,2',2"-(1,3,5-benzenetriyltriethylidyne)tris(hydrazinecarboximidamide); and 2,2'-(1,3-phenylenedipentylidyne)bis(hydrazinecarboximidamide).

The present invention is further directed to a method for treating a mammal suffering from malaria or the sequelae of malarial infection comprising administering a therapeutically effective amount of a compound of the formula:

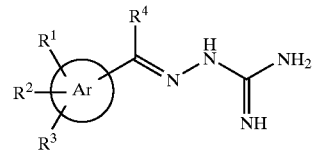

wherein Ar is an aromatic group and $R^1$, $R^2$, and $R^3$ are independently selected from hydrogen, hydroxy, alkoxy, benzyloxy, N-methylthiourea, dialkylamino and an aminodimethylpyrimidinylamino group; wherein $R^4$ is hydrogen or lower alkyl; or a pharmaceutically acceptable salt thereof. Aryl may be, for example, a phenyl, naphthyl, 1,4-dihydro-1,4-dioxo-3-methyl-7-naphthalenyl, benzopyran-4-on-3-yl, quinolinyl or a benzopyrano[2,3-b]pyridine group. Non-limiting examples of salts include hydrochloride, dihydrochloride, sulfate, hemisulfate, and dimethanesulfonate. Preferred compounds include but are not limited to:

2-[(2,3-dihydroxyphenyl)methylene]hydrazinecarboximidamide;

2-[(2-hydroxyphenyl)methylene]hydrazinecarboximidamide;

2-[(2-hydroxy-5-methoxyphenyl)methylene]hydrazinecarboximidamide;

2-[(2-hydroxy-1-naphthyl)methylidene]hydrazinecarboximidamide;

2-[(1-hydroxy-2-naphthyl)ethylidene]hydrazinecarboximidamide;

2-[(2-pyridyl)methylene]hydrazinecarboximidamide;

2-[(4-quinolinyl)methylene]hydrazinecarboximidamide;

2-[(3,4-dihydroxyphenyl)ethylidene]hydrazinecarboximidamide;

2-[(4-hydroxyphenyl)ethylidene]
hydrazinecarboximidamide;
2-[(2-hydroxyphenyl)ethylidene]
hydrazinecarboximidamide;
2-[(2-hydroxy-4-methoxyphenyl)methylene]
hydrazinecarboximidamide;
2-{[2-hydroxy-4-(diethylamino)phenyl]
methylene}hydrazinecarboximidamide;
2-[[3-(3,4-dimethyl-2(3H)-imino-6-pyrimidinyl)phenyl]
ethylidene]hydrazinecarboximidamide;
2-[[4-(3,4-dimethyl-2(3H)-imino-6-pyrimidinyl)phenyl]
ethylidene]hydrazinecarboximidamide;
2-[1-(4-benzyloxy-2-hydroxy-3-methylphenyl)
ethylidene]hydrazinecarboximidamide;
2-amino-3-[(aminoiminomethyl)hydrazono]methyl]-6-
chloro-4H-1-benzopyran-4-one;
2-[(1,4-dihydro-1,4-dioxo-3-methyl-7-naphthalenyl)
ethylidene]hydrazinecarboximidamide;
2-[[1-[(aminoiminomethyl)hydrazono]-1,4-dihydro-3-
methyl-4-oxo-7-naphthalenyl]ethylidene]
hydrazinecarboximidamide;
N-[3-[1-[(aminoiminomethyl)hydrazono]ethyl]phenyl]-
N'-methylthiourea;
2-[(2,3,4-trihydroxyphenyl)methylene]
hydrazinecarboximidamide;
2-[(2,5-dihydroxyphenyl)methylene]
hydrazinecarboximidamide;
2-[(4-hydroxy-3-methoxyphenyl)ethylidene]
hydrazinecarboximidamide;
2-[(3,4-dihydroxy-5-methoxyphenyl)methylene]
hydrazinecarboximidamide;
1-(2-hydroxyethyl)-2-[(2-pyridyl)methylene]
hydrazinecarboximidamide;
2-[[2-hydroxy-4-(diethylamino)phenyl]methylene]
hydrazinecarboximidamide; and
3-[1-[(aminoiminomethyl)hydrazono]ethyl]-2-methyl-
5H-1-benzopyrano[2,3-b]pyridin-5-one.

The invention also provides for a method for treating a mammal suffering from malaria or the sequelae of malarial infection comprising administering a therapeutically effective amount of 2,2'-[(1,4-dihydro-1,4-dioxo-2,3-naphthalenediyl)bis(1-methyl-3-propanyl-1-ylidene)]bis
(hydrazinecarboximidamide);
N,N'-bis[3-[1-[(aminoiminomethyl)hydrazono]ethyl]
phenyl]pentanediamide;
2,6-bis[1-[[(dimethylamino)acetyl]hydrazono]ethyl]
pyridine;
2-[3-(1,4-dihydro-1,4-dioxo-3-methyl-2-naphthalenyl)-1-
methylpropylidene]hydrazinecarboximidamide;
1-[(aminoiminomethyl)hydrazono]-1,4-dihydro-3-
methyl-4-oxonaphthalene;
2,2'-(1,4-cyclohexanediylidene)bis
(hydrazinecarboximidamide);
N-[3-[1-[(aminoiminomethyl)hydrazono]ethyl]phenyl]-
N'-methylthiourea;
or pharmaceutically acceptable salts thereof.

The present invention is further directed to a method for depolymerizing hemozoin in a mammal infected with malaria comprising administering to said mammal a hemozoin-depolymerizing effective amount of a compound of the formula

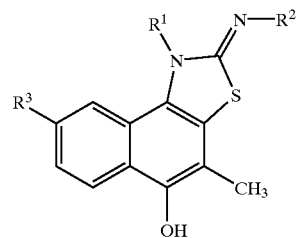

wherein $R^1$ is hydrogen, alkenyl, hydroxy(lower)alkyl, di[(lower)alkyl]amino(lower)alkyl, a heterocyclic group or a lower alkyl group optionally substituted by a heterocyclic group; $R^2$ is cycloalkyl, alkenyl, lower alkyl, hydroxy(lower alkyl), di[hydroxy(lower)alkyl]amino(lower)alkyl, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor. $R^1$ may be for example hydroxyethyl, allyl, dimethylaminopropyl, morpholinopropyl, or an ethyl group. $R^2$ may be for example a cyclohexyl, allyl, phenyl, morpholinopropyl, methylpiperazinopropyl, di(hydroxyethyl)aminopropyl, ethyl, propyl, hydroxyethyl, or 3-[1-(guanylhydrazono) ethyl]phenyl group. Non-limiting examples of salts include hydrochloride, dihydrochloride, sulfate, hemisulfate, and dimethanesulfonate. Non-limiting examples of substituents and preferred compounds are those as described hereinabove.

The present invention also provides for a method for depolymerizing hemozoin in a mammal infected with malaria comprising administering to said mammal a hemozoin-depolymerizing effective amount of a compound of the formula

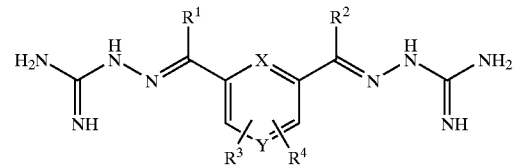

wherein X and Y are independently N or CH, with the proviso that X and Y are not both N; $R^1$ and $R^2$ are both hydrogen or lower alkyl groups; wherein $R^3$ and $R^4$ are independently hydrogen, hydroxy, amino, lower alkoxy, lower alkyl or 1-(guanylhydrazono)alkyl group; or a pharmaceutically acceptable salt thereof. Non-limiting examples of salts include hydrochloride, dihydrochloride, sulfate, hemisulfate, and dimethanesulfonate. Examples of preferred compounds are those as described hereinabove.

A method for depolymerizing hemozoin in a mammal infected with malaria is also provided comprising administering to said mammal a hemozoin-depolymerizing effective amount of a compound of the formula

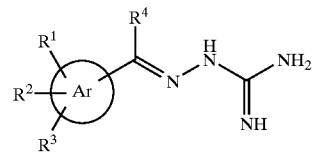

wherein Ar is an aromatic group and $R^1$, $R^2$, and $R^3$ are independently selected from hydrogen, hydroxy, alkoxy, benzyloxy, N-methylthiourea, dialkylamino and an aminodimethylpyrimidinylamino group; wherein $R^4$ is hydrogen or lower alkyl; or a pharmaceutically acceptable salt thereof. Aryl may be, for example, a phenyl, naphthyl, 1,4-dihydro-1,4-dioxo-3-methyl-7-naphthalenyl, benzopyran-4-on-3-yl, quinolinyl or a benzopyrano[2,3-b]pyridine group. Non-limiting examples of salts include hydrochloride, dihydrochloride, sulfate, hemisulfate, and dimethanesulfonate. Non-limiting examples are those described hereinabove.

A method is also provided for depolymerizing hemozoin in a mammal infected with malaria comprising administering to said mammal a hemozoin-depolymerizing effective amount of 2,2'-[(1,4-dihydro-1,4-dioxo-2,3-naphthalenediyl)bis(1-methyl-3-propanyl-1-ylidene)]bis(hydrazinecarboximidamide);

N,N'-bis[3-[1-[(aminoiminomethyl)hydrazono]ethyl]phenyl]pentanediamide;

2,6-bis[1-[[(dimethylamino)acetyl]hydrazono]ethyl]pyridine;

2-[3-(1,4-dihydro-1,4-dioxo-3-methyl-2-naphthalenyl)-1-methylpropylidene]hydrazinecarboximidamide;

1-[(aminoiminomethyl)hydrazono]-1,4-dihydro-3-methyl-4-oxonaphthalene;

2,2'-(1,4-cyclohexanediylidene)bis(hydrazinecarboximidamide);

N-[3-[1-[(aminoiminomethyl)hydrazono]ethyl]phenyl]-N'-methylthiourea;

or pharmaceutically acceptable salts thereof.

A further object of the present invention is to provide a method for ameliorating the adverse effects of hemozoin on host cells comprising administering an effective hemozoin-depolymerizing amount of a compound of formula

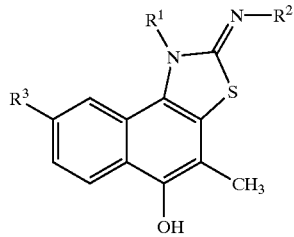

wherein $R^1$ is hydrogen, alkenyl, hydroxy(lower)alkyl, di[(lower)alkyl]amino(lower)alkyl, a heterocyclic group or a lower alkyl group optionally substituted by a heterocyclic group; $R^2$ is cycloalkyl, alkenyl, a lower alkyl group, a hydroxy(lower alkyl) group, a di[hydroxy(lower)alkyl]amino(lower)alkyl group, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor. $R^1$ may be for example hydroxyethyl, allyl, dimethylaminopropyl, morpholinopropyl, or an ethyl group. $R^2$ may be for example a cyclohexyl, allyl, phenyl, morpholinopropyl, methylpiperazinopropyl, di(hydroxyethyl)aminopropyl, ethyl, propyl, hydroxyethyl, or 3-[1-(guanylhydrazono)ethyl]phenyl group. Non-limiting examples of salts include hydrochloride, dihydrochloride, sulfate, hemisulfate, and dimethanesulfonate. Non-limiting examples of substituents and preferred compounds are those as described hereinabove.

A further object of the present invention is to provide a method for ameliorating the adverse effects of hemozoin on host cells comprising administering an effective hemozoin-depolymerizing amount of a compound of formula

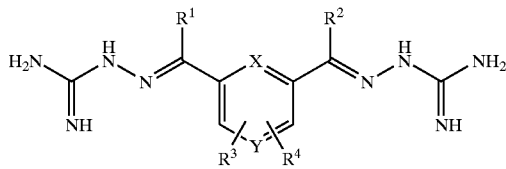

wherein X and Y are independently N or CH, with the proviso that X and Y are not both N; $R^1$ and $R^2$ are both hydrogen or lower alkyl groups; wherein $R^3$ and $R^4$ are independently hydrogen, hydroxy, amino, lower alkoxy, lower alkyl or 1-(guanylhydrazono)alkyl group; or a pharmaceutically acceptable salt thereof. Non-limiting examples of salts include hydrochloride, dihydrochloride, sulfate, hemisulfate, and dimethanesulfonate. Non-limiting examples of preferred compounds are those as described hereinabove.

A further object of the present invention is to provide a method for ameliorating the adverse effects of hemozoin on host cells comprising administering an effective hemozoin-depolymerizing amount of a compound of formula

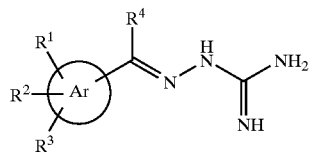

wherein Ar is an aromatic group and $R^1$, $R^2$, and $R^3$ are independently selected from hydrogen, hydroxy, alkoxy, benzyloxy, N-methylthiourea, dialkylamino and an aminodimethylpyrimidinylamino group; wherein $R^4$ is hydrogen or lower alkyl; or a, pharmaceutically acceptable salt thereof. Aryl maybe, for example, a phenyl, naphthyl, 1,4-dihydro-1,4-dioxo-3-methyl-7-naphthalenyl, benzopyran-4-on-3-yl, quinolinyl or a benzopyrano[2,3-b]pyridine group. Non-limiting examples of salts include hydrochloride, dihydrochloride, sulfate, hemisulfate, and dimethanesulfonate. Non-limiting examples of substituents and compounds are those described hereinabove.

A method is also provided for ameliorating the adverse effects of hemozoin on host cells comprising administering an effective hemozoin-depolymerizing amount of 2,2'-[(1,4-dihydro-1,4-dioxo-2,3-naphthalenediyl)bis(1-methyl-3-propanyl-1-ylidene)]bis(hydrazinecarboximidamide);

N,N'-bis[3-[1-[(aminoiminomethyl)hydrazono]ethyl]phenyl]pentanediamide;

2,6-bis[1-[[(dimethylamino)acetyl]hydrazono]ethyl]pyridine;

2-[3-(1,4-dihydro-1,4-dioxo-3-methyl-2-naphthalenyl)-1-methylpropylidene]hydrazinecarboximidamide;

1-[(aminoiminomethyl)hydrazono]-1,4-dihydro-3-methyl-4-oxonaphthalene;

2,2'-(1,4-cyclohexanediylidene)bis(hydrazinecarboximidamide);

N-[3-[1-[(aminoiminomethyl)hydrazono]ethyl]phenyl]-N'-methylthiourea;

or pharmaceutically acceptable salts thereof.

In addition, the present invention is directed to the following anti-malarial compounds or pharmaceutically acceptable salts thereof, and compositions comprising the following compounds:

2,2'-[(4-hydroxy-1,3-phenylene)diethylidyne]bis(hydrazinecarboximidamide);

2,2'-[(2-hydroxy-5-methyl-1,3-phenylene)dimethylidyne]bis(hydrazinecarboximidamide);

2,2'-[(2-methoxy-5-methyl-1,3-phenylene)dimethylidyne]bis(hydrazinecarboximidamide);

N-[3-[1-[(aminoiminomethyl)hydrazono]ethyl]phenyl]-N'-methylthiourea;

2,2'-[(4-hydroxy-1,3-phenylene)dimethylidyne]bis(hydrazinecarboximidamide);

2,6-bis[1-[[(dimethylamino)acetyl]hydrazono]ethyl]pyridine dihydrochloride;

2-(cyclohexylimino)-1,2-dihydro-4-methyl-1-[3-(dimethylamino)propyl]naphtho[1,2-d]thiazol-5-ol;

2-[[3-[1-[2-(aminoiminomethyl)hydrazono]ethyl]phenyl]amino]-4-methylnaphtho[1,2-d]thiazol-5-ol;

2-[[3-(3,4-dimethyl-2(3H)-imino-6-pyrimidinyl)phenyl]ethylidene]hydrazinecarboximidamide;

2-[[4-(3,4-dimethyl-2(3H)-imino-6-pyrimidinyl)phenyl]ethylidene]hydrazinecarboximidamide;

2,2'-(1,3-phenylenediethylidyne)bis(N-hydroxyhydrazinecarboximidamide);

2-[1-(4-benzyloxy-2-hydroxy-3-methylphenyl)ethylidene]hydrazinecarboximidamide;

2-[[2-hydroxy-4-(diethylamino)phenyl]methylene]hydrazinecarboximidamide;

4-methyl-2-[[3-(4-morpholino)propyl]amino]naphtho[1,2-d]thiazol-5-ol; and

8-[1-[2-(aminoiminomethyl)hydrazono]ethyl]-2-(butylimino)-1,2-dihydro-1,4-dimethylnaphtho[1,2-d]thiazol-5-ol.

It is thus an object of the present invention to provide a method for treating a mammal suffering from malaria and treating the sequelae of malarial infection.

It is a further object of the present invention to provide a method for depolymerizing hemozoin in a mammal infected with malaria comprising administering to said mammal a hemozoin-depolymerizing effective amount of a compound of the present invention.

It is yet a further object of the present invention to provide a method for ameliorating the adverse effects of hemozoin on host cells comprising administering an effective hemozoin-depolymerizing amount of a compound the present invention.

These and other aspects of the present invention will be better appreciated by reference to the following drawing and Detailed Description.

DETAILED DESCRIPTION OF THE INVENTION

Figure 1:
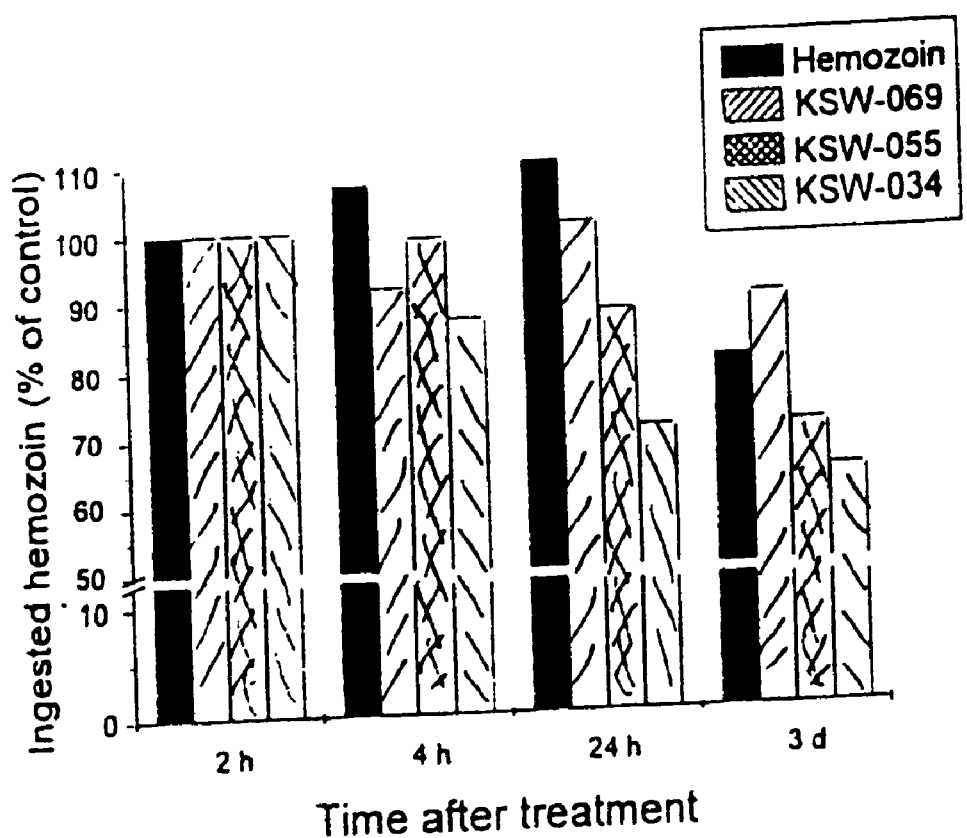
FIG. 1 depicts the effect of various compounds of the present invention on the breakdown of macrophage-ingested hemozoin.

The present invention is directed to compounds, compositions and methods for increasing the toxicity of hemozoin towards malaria parasites and reducing its toxicity towards the host. As described above, heme and its derivatives readily undergo redox chemistry generating toxic free radicals; malaria parasites, survive during hemoglobin catabolism by polymerizing heme into a non-toxic polymer called hemozoin which accumulates in the food vacuole of the parasite and is released into the circulation when the parasites exit the ruptured erythrocyte. Depolymerization of hemozoin will generate increase levels of heme toxic to the parasite.

Furthermore, hemozoin released from erythrocytes is taken up by host cells and induces a variety of serious adverse sequelae which may persist far beyond the period. of infection. This long-lived polymer induces cytokine production in macrophages which induce a range of effects including anemia, immunosuppression, and failure to gain weight. Depolymerizing hemozoin within host cells reduces the toxicity of hemozoin; host cells are capable of destroying the freed heme by the enzyme heme oxygenase.

Certain of the compounds of the present invention generally fall into two broad categories: naphthothiazolium salts, and aromatic guanylhydrazones. The aromatic guanylhydrazones are further divided into aromatic groups with one or two guanylhydrazone groups. As will be described below, certain of these compounds are known in the art, and others are novel.

In accordance with the present invention, a method is provided for treating a mammal suffering from malaria or the sequelae of malarial infection comprising administering a therapeutically effective amount of a compound of the formula:

wherein $R^1$ is hydrogen, alkenyl, hydroxy(lower)alkyl, di[(lower)alkyl]amino(lower)alkyl, a heterocyclic group or a lower alkyl group optionally substituted by a heterocyclic group; $R^2$ is cycloalkyl, alkenyl, lower alkyl, a hydroxy (lower alkyl), di[hydroxy(lower)alkyl]amino(lower)alkyl, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor.

The lower alkyl groups referred to above contain 1–6 carbon atoms and include methyl, ethyl, propyl, butyl, pentyl, hexyl, and the corresponding branched-chain isomers thereof. The alkenyl groups contain from 2 to 6 straight chain or branched carbon atoms, with a single double bond, such as vinyl, allyl, and the like. Similarly, the alkoxy groups contain from 1 to 6 carbon atoms, and include methoxy, ethoxy, propoxy, butoxy, pentoxy, and hexoxy, and the corresponding branched-chain isomers thereof. The hydroxy (lower)alkyl groups comprise the lower alkyl groups with a hydroxy substitution. Di[(lower)alkyl]amino(lower)alkyl groups include, for example, dimethylaminopropyl, diethylaminopropyl, diethylaminobutyl, dimethylaminopentyl, methylpiperazinopropyl, di(hydroxyethyl)aminopropyl, and morpholinopropyl.

Heterocyclic groups referred to herein include 4–8 membered rings having at least one and up to 3 heteroatoms, e.g., oxygen, nitrogen, or sulfur, therein, and including various degrees of unsaturation. Representatives of such heterocyclic groups are those such as isoxazolyl, phenylisoxazolyl, furanyl, morpholino, thiomorpholino, pyrimidinyl, piperidino, homopiperidino, piperazino, methylpiperazino, hexamethyleneimino, tetrahydroquinolyl, pyridyl, methylpyridyl, imidazolyl, pyrrolidinyl, 2,6-dimethylmorpholino, 1,2,4-triazoylyl, thiazolyl, thiophenyl, thiazolinyl, methylthiazolyl, and the like.

$R^1$ may be for example hydroxyethyl, allyl, morpholinopropyl, methylpiperazinopropyl, dimethylaminopropyl, or an ethyl group. $R^2$ may be for example a cyclohexyl, allyl, phenyl, di(hydroxyethyl)aminopropyl, ethyl, propyl, hydroxyethyl, or 3-[1-(guanylhydrazono)ethyl]phenyl group. Preferred compounds include but are not limited to:

- 1-ethyl-2-(ethylimino)-1,2-dihydro-4-methylnaphtho[1,2-d]-thiazol-5-ol;
- 1,2-dihydro-1,4-dimethyl-2-[[3-(4-methyl-1-piperazinyl)propyl]imino]naphtho[1,2-d]thiazol-5-ol;
- 2-(cyclohexylimino)-1,2-dihydro-4-methyl-1-[3-(dimethylamino)propyl]naphtho[1,2-d]thiazol-5-ol;
- 2-[[3-[1-(2-(aminoiminomethyl)hydrazono]ethyl]phenyl]amino]-4-methylnaphtho[1,2-d]thiazol-5-ol;
- 2-[[3-[bis(2-hydroxyethyl)amino]propyl]imino]-1,2-dihydro-1,4-dimethylnaphtho[1,2-d]thiazol-5-ol;
- 1,2-dihydro-4-methyl-1-(2-propenyl)-2-(2-propenylimino)naphtho[1,2-d]thiazol-5-ol;
- 4-methyl-2-(2-propenylamino)naphtho[1,2-d]thiazol-5-ol;
- 2-(cyclohexylimino)-5-hydroxy-4-methylnaphtho[1,2-d]thiazole-1(2H)-ethanol;
- 1,2-dihydro-2-[(2-hydroxyethyl)imino]-1,4-dimethylnaphtho[1,2-d]thiazol-5-ol;
- 1,2-dihydro-1,4-dimethyl-2-(phenylimino)naphtho[1,2-d]thiazol-5-ol;
- 1,2-dihydro-4-methyl-2-(phenylimino)naphtho[1,2-d]thiazol-5-ol;
- 4-methyl-2-[[3-(4-morpholino)propyl]amino]naphtho[1,2-d]thiazol-5-ol;
- 8-[1-[2-(aminoiminomethyl)hydrazono]ethyl]-2-(butylimino)-1,2-dihydro-1,4-dimethylnaphtho[1,2-d]thiazol-5-ol;
- 2-(cyclohexylimino)-1,2-dihydro-4-methyl-1-[3-(4-morpholino)propyl]naphtho[1,2-d]thiazol-5-ol;
- 2-(cyclohexylimino)-1,2-dihydro-4-methyl-1-[3-(4-methyl-1-piperazinyl)propyl]naphtho[1,2-d]thiazol-5-ol;
- 2-[[3-(dimethylamino)propyl]imino]-1,2-dihydro-1,4-dimethylnaphtho[1,2-d]thiazol-5-ol;
- 1,2-dihydro-4-methyl-1-[3-(dimethylamino)propyl]-2-(1-methylethyl)aminonaphtho[1,2-d]thiazol-5-ol;

or pharmaceutically acceptable salts of the above.

For the purposes of this invention, the compounds are uncharged or biologically and pharmaceutically acceptable salts. Useful salt forms include but are not limited to the halides, particularly the hydrobromide, hydrochloride, sulfate, hemisulfate, tosylate, methanesulfonate, and mesitylenesulfonate salts. As several of the compounds described herein have multiple charges, suitable salts may include combinations of salts, such as both hydrochloride and hydrobromide, or, for example, a dihydrochloride, dihydrobromide, or trihydrochloride. Other related salts can be formed using similarly non-toxic, and biologically and pharmaceutically acceptable anions.

The present invention is also directed to a method for treating a mammal suffering from malaria or the sequelae of malaria infection comprising administering a therapeutically effective amount of a compound of the formula:

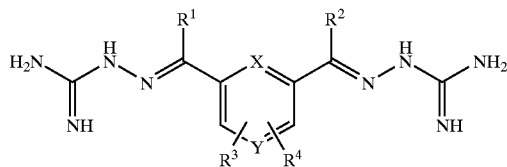

wherein X and Y are independently N or CH, with the proviso that X and Y are not both N; $R^1$ and $R^2$ are both hydrogen or lower alkyl groups; wherein $R^3$ and $R^4$ are independently hydrogen, hydroxy, amino, lower alkoxy, lower alkyl or 1-(guanylhydrazono)alkyl group; or a pharmaceutically acceptable salt thereof.

The lower alkyl groups are those as defined hereinabove. Preferred compounds include but are not limited to:

- 2,2'-[(4,6-dihydroxy-1,3-phenylene)diethylidyne]bis(hydrazinecarboximidamide);
- 2,2'-[(4-hydroxy-1,3-phenylene)diethylidyne]bis(hydrazinecarboximidamide);
- 2,2'-(1,3-phenylenediethylidyne)bis(hydrazinecarboximidamide);
- 2,2'-[(2-hydroxy-5-methyl-1,3-phenylene)dimethylidyne]bis(hydrazinecarboximidamide);
- 2,2'-[(2-methoxy-5-methyl-1,3-phenylene)dimethylidyne]bis(hydrazinecarboximidamide);
- 2,2'-[(2-amino-1,3-phenylene)diethylidyne]bis(hydrazinecarboximidamide);
- 2,2'-[(4-hydroxy-1,3-phenylene)dimethylidyne]bis(hydrazinecarboximidamide);
- 2,2'-(1,3-phenylenedimethylidyne)bis(hydrazinecarboximidamide);
- 2,2'-(2,6-pyridinediyldiethylidyne)bis(hydrazinecarboximidamide);
- 2,2'-(3,5-pyridinediyldiethylidyne)bis(hydrazinecarboximidamide);
- 2,2'-[(2,6-dimethyl-3,5-pyridinediyl)diethylidyne]bis(hydrazinecarboximidamide);
- 2,6-bis[1-[[(dimethylamino)acetyl]hydrazono]ethyl]pyridine;
- 2,2'-[(5-amino-1,3-phenylene)diethylidyne]bis(hydrazinecarboximidamide);
- 2,2'-[(5-hydroxy-1,3-phenylene)diethylidyne]bis(hydrazinecarboximidamide);
- 2,2',2''-(1,3,5-benzenetriyltriethylidyne)tris(hydrazinecarboximidamide); and
- 2,2'-(1,3-phenylenedipentylidyne)bis(hydrazinecarboximidamide);

and pharmaceutically acceptable salts thereof.

The present invention is further directed to a method for treating a mammal suffering from malaria or the sequelae of malarial infection comprising administering a therapeutically effective amount of a compound of the formula:

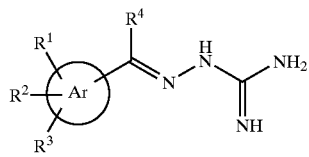

wherein Ar is an aromatic group and $R^1$, $R^2$, and $R^3$ are independently selected from hydrogen, hydroxy, alkoxy, benzyloxy, N-methylthiourea, dialkylamino and a dihydrodimethyliminopyrimidinylamino group; wherein $R^4$ is hydrogen or lower alkyl; or a pharmaceutically acceptable salt thereof.

The aromatic group abbreviated Ar may be aromatic, such as benzene or naphthalene, or a heteroaromatic group. Heterocyclic groups referred to herein include 4–8 membered rings having at least one and up to 3 heteroatoms, e.g., oxygen, nitrogen, or sulfur, therein, and including various degrees of unsaturation. Representatives of such heterocyclic groups are those such as isoxazolyl, phenylisoxazolyl, furanyl, morpholino, thiomorpholino, pyrimidinyl, piperidino, homopiperidino, piperazino, methylpiperazino, hexamethyleneimino, tetrahydroquinolyl, pyridyl, methylpyridyl, imidazolyl, pyrrolidinyl, 2,6-dimethylmorpholino, 1,2,4-triazoylyl, thiazolyl, thiophenyl, thiazolinyl, methylthiazolyl, and the like. The alkoxy and lower alkyl groups are as defined hereinabove. Preferred aryl groups include, for example, a phenyl, naphthyl, 1-[(aminoiminomethyl)hydrazono]-1,4-dihydro-1,4-dioxo-3-methyl-7-naphthalenyl, benzopyran-4-on-3-yl, quinolinyl or a benzopyrano[2,3-b]pyridine group.

Non-limiting examples of compounds include:

2-[(2,3-dihydroxyphenyl)methylene]hydrazinecarboximidamide;

2-[(2-hydroxyphenyl)methylene]hydrazinecarboximidamide;

2-[(2-hydroxy-5-methoxyphenyl)methylene]hydrazinecarboximidamide;

2-[(2-hydroxy-1-naphthyl)methylidene]hydrazinecarboximidamide;

2-[(2-hydroxy-2-naphthyl)ethylidene]hydrazinecarboximidamide;

2-[(2-pyridyl)methylene]hydrazinecarboximidamide;

2-[(4-quinolinyl)methylene]hydrazinecarboximidamide;

2-[(3,4-dihydroxyphenyl)ethylidene]hydrazinecarboximidamide;

2-[(4-hydroxyphenyl)ethylidene]hydrazinecarboximidamide;

2-[(2-hydroxyphenyl)ethylidene]hydrazinecarboximidamide;

2-[(2-hydroxy-4-methoxyphenyl)methylene]hydrazinecarboximidamide;

2-{[2-hydroxy-4-(diethylamino)phenyl]methylene}hydrazinecarboximidamide;

2-[(3-(3,4-dimethyl-2(3H)-imino-6-pyrimidinyl)amino]phenyl)ethylidene]hydrazinecarboximidamide;

2-[(4-[(3,4-dimethyl-2(3H)-imino-6-pyrimidinyl)amino]phenyl)ethylidene]hydrazinecarboximidamide;

2-[1-(4-benzyloxy-2-hydroxy-3-methylphenyl)ethylidene]hydrazinecarboximidamide;

2-amino-3-[(aminoiminomethyl)hydrazono]methyl]-6-chloro-4H-1-benzopyran-4-one;

2-[(1,4-dihydro-1,4-dioxo-3-methyl-7-naphthalenyl)ethylidene]hydrazinecarboximidamide;

2-[[1-[(aminoiminomethyl)hydrazono]-1,4-dihydro-3-methyl-4-oxo-7-naphthalenyl]ethylidene]hydrazinecarboximidamide;

N-[3-[1-[(aminoiminomethyl)hydrazono]ethyl]phenyl]-N'-methylthiourea;

2-[(2,3,4-trihydroxyphenyl)methylene]hydrazinecarboximidamide;

2-[(2,5-dihydroxyphenyl)methylene]hydrazinecarboximidamide;

2-[(4-hydroxy-3-methoxyphenyl)ethylidene]hydrazinecarboximidamide;

2-[(3,4-dihydroxy-5-methoxyphenyl)methylene]hydrazinecarboximidamide;

1-(2-hydroxyethyl)-2-[(2-pyridyl)methylene]hydrazinecarboximidamide;

2-[[2-hydroxy-4-(diethylamino)phenyl]methylene]hydrazinecarboximidamide; and

3-[1-[(aminoiminomethyl)hydrazono]ethyl]-2-methyl-5H-1-benzopyrano[2,3-b]pyridin-5-one.

The present invention is further directed to a method for treating a mammal suffering from malaria or the sequelae of malarial infection comprising administering a therapeutically effective amount of 2,2'-[(1,4-dihydro-1,4-dioxo-2,3-naphthalenediyl)bis(1-methyl-3-propanyl-1-ylidene)]bis(hydrazinecarboximidamide);

N,N'-bis[3-[1-[(aminoiminomethyl)hydrazono]ethyl]phenyl]pentanediamide;

2,6-bis[1-[[(dimethylamino)acetyl]hydrazono]ethyl]pyridine;

2-[3-(1,4-dihydro-1,4-dioxo-3-methyl-2-naphthalenyl)-1-methylpropylidene]hydrazinecarboximidamide;

1-[(aminoiminomethyl)hydrazono]-1,4-dihydro-3-methyl-4-oxonaphthalene;

2,2'-(1,4-cyclohexanediylidene)bis(hydrazinecarboximidamide);

N-[3-[1-[(aminoiminomethyl)hydrazono]ethyl]phenyl]-N'-methylthiourea;

or pharmaceutically acceptable salts thereof.

As will be noted below, a further aspect of the present invention is a method for depolymerizing hemozoin in a mammal infected with malaria comprising administering to said mammal a hemozoin-depolymerizing effective amount of a compound of the formula

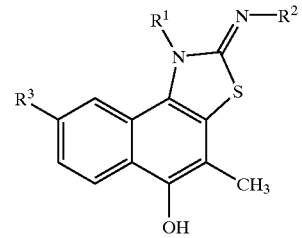

wherein $R^1$ is hydrogen, alkenyl, hydroxy(lower)alkyl, di[(lower)alkyl]amino(lower)alkyl, a heterocyclic group or a lower alkyl group optionally substituted by a heterocyclic group; $R^2$ is cycloalkyl, alkenyl, lower alkyl, hydroxy(lower alkyl), di[hydroxy(lower)alkyl]amino(lower)alkyl, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor. Non-limiting examples of substituents and preferred compounds are those as described hereinabove.

A method is provided for depolymerizing hemozoin in a mammal infected with malaria comprising administering to said mammal a hemozoin-depolymerizing effective amount of a compound of the formula

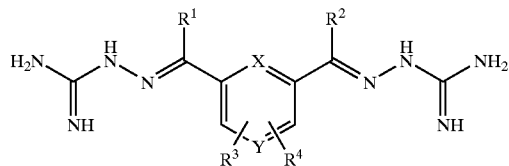

wherein X and Y are independently N or CH, with the proviso that X and Y are not both N; $R^1$ and $R^2$ are both hydrogen or lower alkyl groups; wherein $R^3$ and $R^4$ are independently hydrogen, hydroxy, amino, lower alkoxy, lower alkyl or 1-(guanylhydrazono)alkyl group; or a pharmaceutically acceptable salt thereof. Non-limiting examples of preferred compounds are those as described hereinabove.

A method is provided for depolymerizing hemozoin in a mammal infected with malaria comprising administering to said mammal a hemozoin-depolymerizing effective amount of a compound of the formula

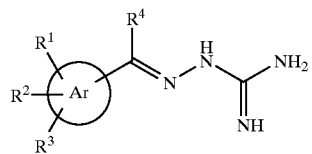

wherein Ar is an aromatic group and $R^1$, $R^2$ and $R^3$ are independently selected from hydrogen, hydroxy, alkoxy, benzyloxy, N-methylthiourea, dialkylamino and an aminodimethylpyrimidinylamino group; wherein $R^4$ is hydrogen or lower alkyl; or a pharmaceutically acceptable salt thereof. Non-limiting examples of substituents and compounds are those described hereinabove.

The present invention is also directed to a method for depolymerizing hemozoin in a mammal infected with malaria comprising administering to said mammal a hemozoin-depolymerizing effective amount of 2,2'-[(1,4-dihydro-1,4-dioxo-2,3-naphthalenediyl)bis(1-methyl-3-propanyl-1-ylidene)]bis(hydrazinecarboximidamide);

N,N'-bis[3-[1-[(aminoiminomethyl)hydrazono]ethyl]phenyl]pentanediamide;

2,6-bis[1-[[(dimethylamino)acetyl]hydrazono]ethyl]pyridine;

2-[3-(1,4-dihydro-1,4-dioxo-3-methyl-2-naphthalenyl)-1-methylpropylidene]hydrazinecarboximidamide;

1-[(aminoiminomethyl)hydrazono]-1,4-dihydro-3-methyl-4-oxonaphthalene;

2,2'-(1,4-cyclohexanediylidene)bis(hydrazinecarboximidamide);

N-[3-[1-[(aminoiminomethyl)hydrazono]ethyl]phenyl]-N'-methylthiourea;

or pharmaceutically acceptable salts thereof.

A further invention herein comprises a method for ameliorating the adverse effects of hemozoin on host cells comprising administering an effective hemozoin-depolymerizing amount of a compound of formula

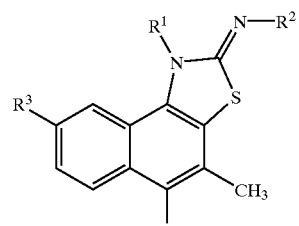

wherein $R^1$ is hydrogen, alkenyl, hydroxy(lower)alkyl, di[(lower)alkyl]amino(lower)alkyl, a heterocyclic group or a lower alkyl group optionally substituted by a heterocyclic group; $R^2$ is cycloalkyl, alkenyl, lower alkyl, hydroxy(lower alkyl), di[hydroxy(lower)alkyl]amino(lower)alkyl, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor. Non-limiting examples of substituents and preferred compounds are those as described hereinabove.

A further invention herein comprises a method for ameliorating the adverse effects of hemozoin on host cells comprising administering an effective hemozoin-depolymerizing amount of a compound of formula

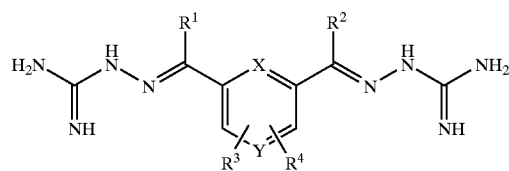

wherein X and Y are independently N or CH, with the proviso that X and Y are not both N; $R^1$ and $R^2$ are both hydrogen or lower alkyl groups; wherein $R^3$ and $R^4$ are independently hydrogen, hydroxy, amino, lower alkoxy, lower alkyl or 1-(guanylhydrazono)alkyl group; or a pharmaceutically acceptable salt thereof. Non-limiting examples of preferred compounds are those as described hereinabove.

Yet a further invention herein comprises a method for ameliorating the adverse effects of hemozoin on host cells comprising administering an effective hemozoin-depolymerizing amount of a compound of formula
wherein Ar is an aromatic group and $R^1$, $R^2$ and $R^3$ are independently selected from

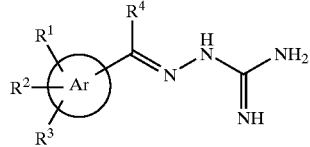

hydrogen, hydroxy, alkoxy, benzyloxy, N-methylthiourea, dialkylamino and an aminodimethylpyrimidinylamino group; wherein $R^4$ is hydrogen or lower alkyl; or a pharmaceutically acceptable salt thereof. Non-limiting examples of substituents and compounds are those described hereinabove.

A still further invention herein comprises a method for ameliorating the adverse effects of hemozoin on host cells comprising administering an effective hemozoin-depolymerizing amount of 2,2'-[(1,4-dihydro-1,4-dioxo-2,3-naphthalenediyl)bis(1-methyl-3-propanyl-1-ylidene)]bis(hydrazinecarboximidamide);

N,N'-bis[3-[1-[(aminoiminomethyl)hydrazono]ethyl] phenyl]pentanediamide;

2,6-bis[1-[[(dimethylamino)acetyl]hydrazono]ethyl] pyridine;

2-[3-(1,4-dihydro-1,4-dioxo-3-methyl-2-naphthalenyl)-1-methylpropylidene]hydrazinecarboximidamide;

1-[(aminoiminomethyl)hydrazono]-1,4-dihydro-3-methyl-4-oxonaphthalene;

2,2'-(1,4-cyclohexanediylidene)bis(hydrazinecarboximidamide);

N-[3-[1-[(aminoiminomethyl)hydrazono]ethyl]phenyl]-N'-methylthiourea;

or pharmaceutically acceptable salts thereof.

Certain of the compounds of the present invention are novel. The present invention is directed to these compounds as well as to compositions, including pharmaceutical compositions, comprising these compounds. Such compounds include but are not limited to:

2,2'-[(4-hydroxy-1,3-phenylene)diethylidyne]bis(hydrazinecarboximidamide);

2,2'-[(2-hydroxy-5-methyl-1,3-phenylene) dimethylidyne]bis(hydrazinecarboximidamide);

2,2'-[(2-methoxy-5-methyl-1,3-phenylene) dimethylidyne]bis(hydrazinecarboximidamide);

N-[3-[1-[(aminoiminomethyl)hydrazono]ethyl]phenyl]-N'-methylthiourea;

2,2'-[(4-hydroxy-1,3-phenylene)dimethylidyne]bis(hydrazinecarboximidamide);

2,6-bis[1-[[(dimethylamino)acetyl]hydrazono]ethyl] pyridine dihydrochloride;

2-(cyclohexylimino)-1,2-dihydro-4-methyl-1-[3-(dimethylamino)propyl]naphtho[1,2-d]thiazol-5-ol;

2-[[3-[1-[2-(aminoiminomethyl)hydrazono]ethyl]phenyl] amino]-4-methylnaphtho[1,2-d]thiazol-5-ol;

2-[[3-(3,4-dimethyl-2(3H)-imino-6-pyrimidinyl)phenyl] ethylidene]hydrazinecarboximidamide;

2-[[4-(3,4-dimethyl-2(3H)-imino-6-pyrimidinyl)phenyl] ethylidene]hydrazinecarboximidamide;

2,2'-(1,3-phenylenediethylidyne)bis(N-hydroxyhydrazinecarboximidamide);

2-[1-(4-benzyloxy-2-hydroxy-3-methylphenyl) ethylidene]hydrazinecarboximidamide;

2-[[2-hydroxy-4-(diethylamino)phenyl]methylene] hydrazinecarboximidamide;

4-methyl-2-[[3-(4-morpholino)propyl]amino]naphtho[1,2-d]thiazol-5-ol; and

8-[1-[2-(aminoiminomethyl)hydrazono]ethyl]-2-(butylimino)-1,2-dihydro-1,4-dimethylnaphtho[1,2-d] thiazol-5-ol;

and their pharmaceutically acceptable salts.

With regard generally to the synthesis of naphthothiazolium salts, they may be prepared based on the method of Lau and Gompf (29), as modified by Ulrich and Cerami (20) which involves reaction of a 2-fold excess of a 1,4-quinone such as 2-methyl-1,4-naphthoquinone (menadione) with an N-substituted or an N,N'-disubstituted thiourea derivative in ethanol in the presence of 1 equivalent of hydrochloric acid at room temperature in the dark, typically for 24–48 hrs. If amine functions are present in the side chain, sufficient additional hydrochloric acid is added to neutralize them. Often the crude product separates out overnight and can be filtered and recrystallized from a suitable solvent system such as ethanol-ethyl acetate. If product does not separate from the initial reaction mixture after several days, it is concentrated and treated with ethyl acetate or ether to induce crystallization.

Many substituted thioureas are commercially available as starting materials. Others are conveniently synthesized (13) by reacting an alkyl or aryl isothiocyanate with ammonia (for monosubstituted thioureas) or a primary amine (for disubstituted thioureas) in ether or isopropanol. If solid product does not separate out within 16 hr, the solvent is evaporated and the crude thiourea derivative is triturated with ether to induced crystallization. Thioureas so produced are of satisfactory purity for naphthothiazolium synthesis without further purification.

One of the following three schemes may be employed to prepare naphthothiazolium salts of the following general formula:

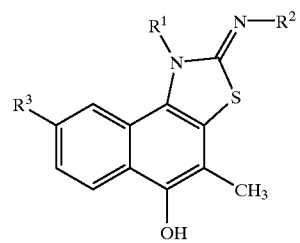

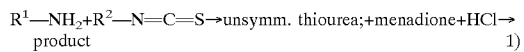

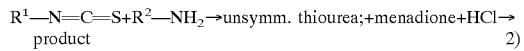

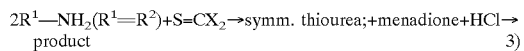

In Scheme 1), a (disubstituted amino)alkyl amine, $R^1$—$NH_2$, is reacted with a secondary alkyl or aryl isothiocyanate, $R^2$—S=C=N, to give an unsymmetrical 1,3-disubstituted thiourea. In Scheme 2), a secondary alkyl or aryl amine, $R^2$—$NH_2$, is reacted with a (disubstituted amino)alkyl isothiocyanate, R—N=C=S, also to give an unsymmetrical 1,3-disubstituted thiourea. In Scheme 3), two equivalents of a (disubstituted amino)alkyl amine, $R^1$—$NH_2$, are reacted with one equivalent of 1,1'-thiocarbonyldiimidazole, to give a symmetric 1,3-bis (aminoalkyl)thiourea.

The following reactants are commercially available for carrying out the above reactions:

ω-(Disubst. amino) or hydroxyalkyl primary $R^1$—$NH_2$: 2-(dimethylamino)ethylamine; 3-(dimethylamino) propylamine; 4-(dimethylamino)butylamine; 5-(dimethylamino)pentylamine; 3-(diethylamino) propylamine; 3-(dibutylamino)propylamine; 3-[bis(2-hydroxyethyl)amino]propylamine; 3-(dimethylamino)-2,2-dimethylpropylamine; 2-(1-pyrrolidino)ethylamine; 2-(1-methyl-2-pyrrolidino)ethylamine; 3-(1-pyrrolidino) propylamine; 3-(4-morpholino)propylamine; 2-(4-morpholino)ethylamine; 2-(1-piperidino)ethylamine; 3-(4-methylpiperazin-1-yl)propylamine; 3-(1-imidazolyl) propylamine; 2-(2-pyridinyl)ethylamine; 2-hydroxyethylamine; 3-hydroxypropylamine; 4-hydroxybutylamine; and 2-(2-hydroxyethoxy)ethylamine.

Selected secondary alkyl $R^2$—N=C=S: cyclopentyl isothiocyanate; cyclohexyl isothiocyanate; cyclooctyl isothiocyanate; cyclododecyl isothiocyanate; isopropyl isothiocyanate; phenyl isothiocyanate; 4-chlorophenyl isothiocyanate; 4-methoxyphenyl isothiocyanate;

4-dimethylaminophenyl isothiocyanate; 3-acetylphenyl isothiocyanate; and 4-acetylphenyl isothiocyanate.

ω-(Disubstituted amino) $R^1$—N═C═S: 3-(diethylamino)propyl isothiocyanate; 2-(4-morpholino)ethyl isothiocyanate; 3-(4-morpholino)propyl isothiocyanate; and 2-(1-piperidino)ethyl isothiocyanate.

Selected secondary alkyl/aryl $R^2$—$NH_2$: 2-amino-5-diethylaminopentane; 4-amino-1-benzylpiperidine; 4-amino-2,2,6,6-tetramethylpiperidine; 2-aminoadamantane (+)-2-amino-1-propanol; (−)-2-amino-1-propanol; 2-aminoindane; and 4-aminopyridine.

By following the aforementioned methods, the following compounds may be prepared:

1-ethyl-2-(ethylimino)-1,2-dihydro-4-methylnaphtho[1,2-d]thiazol-5-ol monohydrochloride;

1,2-dihydro-1,4-dimethyl-2-[[3-(4-methyl-1-piperazinyl)propyl]imino]naphtho[1,2-d]thiazol-5-ol trihydrochloride;

2-(cyclohexylimino)-1,2-dihydro-4-methyl-1-[3-(dimethylamino)propyl]naphtho[1,2-d]thiazol-5-ol dihydrochloride;

2-[[3-[1-[2-(aminoiminomethyl)hydrazono]ethyl]phenyl]amino]-4-methylnaphtho[1,2-d]thiazol-5-ol dihydrochloride;

2-[[3-[bis(2-hydroxyethyl)amino]propyl]imino]-1,2-dihydro-1,4-dimethylnaphtho[1,2-d]thiazol-5-ol dihydrochloride;

1,2-dihydro-4-methyl-1-(2-propenyl)-2-(2-propenylimino)naphtho[1,2-d]thiazol-5-ol monohydrochloride;

4-methyl-2-(2-propenylamino)naphtho[1,2-d]thiazol-5-ol monohydrochloride;

2-(cyclohexylimino)-5-hydroxy-4-methylnaphtho[1,2-d]thiazole-1(2H)-ethanol monohydrochloride;

1,2-dihydro-2-[(2-hydroxyethyl)imino]-1,4-dimethylnaphtho[1,2-d]thiazol-5-ol monohydrochloride;

1,2-dihydro-1,4-dimethyl-2-(phenylimino)naphtho[1,2-d]thiazol-5-ol monohydrochloride;

1,2-dihydro-4-methyl-2-(phenylimino)naphtho[1,2-d]thiazol-5-ol monohydrochloride;

4-methyl-2-[[3-(4-morpholino)propyl]amino]naphtho[1,2-d]thiazol-5-ol dihydrochloride;

8-[1-[2-(aminoiminomethyl)hydrazono]ethyl]-2-(butylimino)-1,2-dihydro-1,4-dimethylnaphtho[1,2-d]thiazol-5-ol monohydrochloride;

1-(3-dimethylaminopropyl)-2-cyclohexylamino-5-hydroxy-4-methylnaphtho[1,2-d]thiazolium chloride hydrochloride;

2-(3-(4-morpholino)propylamino)-4-methyl-5-hydroxynaphtho[1,2-d]thiazolium chloride hydrochloride;

2-(cyclohexylimino)-1,2-dihydro-4-methyl-1-[3-(4-morpholino)propyl]naphtho[1,2-d]thiazol-5-ol dihydrochloride;

2-(cyclohexylimino)-1,2-dihydro-4-methyl-1-[3-(4-methyl-1-piperazinyl)propyl]naphtho[1,2-d]thiazol-5-ol trihydrochloride;

2-[[3-(dimethylamino)propyl]imino]-1,2-dihydro-1,4-dimethylnaphtho[1,2-d]thiazol-5-ol dihydrochloride;

1,2-dihydro-1,4-dimethyl-2-[(2-phenylethyl)imino]naphtho[1,2-d]thiazol-5-ol monohydrochloride;

1,2-dihydro-1,4-dimethyl-2-(octylimino)naphtho[1,2-d]thiazol-5-ol monohydrochloride;

2-(butylimino)-1,2-dihydro-1,4-dimethylnaphtho[1,2-d]thiazol-5-ol monohydrochloride;

1,2-dihydro-2-[(2-methoxyethyl)imino]-1,4-dimethylnaphtho[1,2-d]thiazol-5-ol monohydrochloride;

1-hexyl-2-(hexylimino)-1,2-dihydro-4-methylnaphtho[1,2-d]thiazol-5-ol monohydrochloride;

1-butyl-2-(butylimino)-1,2-dihydro-4-methylnaphtho[1,2-d]thiazol-5-ol monohydrochloride;

1,2-dihydro-4-methyl-1-(2-methylpropyl)-2-[(2-methylpropyl)imino]naphtho[1,2-d]thiazol-5-ol monohydrochloride;

1,2-dihydro-4-methyl-1-propyl-2-(propylimino)naphtho[1,2-d]thiazol-5-ol monohydrochloride;

1,2-dihydro-1,4-dimethyl-2-(methylimino)naphtho[1,2-d]thiazol-5-ol monohydrochloride;

2-[(4-methoxyphenyl)amino]-4-methylnaphtho[1,2-d]thiazol-5-ol monohydrochloride;

9,10,11,12-tetrahydro-5-hydroxy-6-methylnaphtho[1',2':4,5]thiazolo[3,2-a]pyrimidine monohydrochloride;

9,10-dihydro-5-hydroxy-6-methyl-11H-imidazo[2,1-b]naphtho[1,2-d]thiazole monohydrochloride;

5-hydroxy-4-methyl-2-(phenylimino)naphtho[1,2-d]thiazole-1(2H)-ethanol monohydrochloride; and 1-[3-[[5-hydroxy-1,4-dimethylnaphtho[1,2-d]thiazol-2(1H)-ylidene]amino]phenyl]ethanone.

With regard to the aromatic guanylhydrazones of the present invention, these compounds include aromatic groups with a single guanylhydrazone group and those with two guanylhydrazone groups (i.e., a bisguanylhydrazone). Examples are shown below:

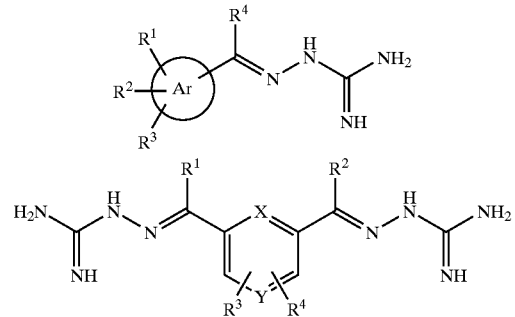

Hydrazones of aromatic ketones and aldehydes are conveniently made by reaction of the ketone or aldehyde with a slight excess the corresponding hydrazine derivative, typically in alcoholic solvent with heating for several hours, for example, as described (13,14). Examples of typical procedures are provided below.

Synthesis of 5-(1-[2-(aminoiminomethyl)hydrazono] ethyl)salicylic acid hydrochloride. 5-Acetylsalicylic acid (3.6 g) and aminoguanidine hydrochloride (2.4 g) were heated in 80% ethanol (25 mL) for 2 hr. Cooling and filtration gave 5.2 g of crude 5-(1-[2-(aminoiminomethyl) hydrazono]ethyl)salicylic acid hydrochloride. Of this, 0.58 g was purified by dissolving in aq. NaOH (pH 12.5) and reprecipitation with aq HCl (to pH 2) to give 0.45 g of 5-(1-[2-(aminoiminomethyl)hydrazono]ethyl)salicylic acid hydrochloride, mp 312–3° C. (dec).

Synthesis of 2-[(3,4-dihydroxyphenyl)ethylidyne] hydrazinecarboximidamide hydrochloride. 3,4-dihydroxyacetophenone (3.04 g) and aminoguanidine hydrochloride (2.44 g) were heated in 75% ethanol (16 mL)

for 4 hr under nitrogen. Cooling and filtration gave 2.7 g of 2-[(3,4-dihydroxyphenyl)ethylidyne] hydrazinecarboximidamide hydrochloride, mp 242–5° C.

Preparation of 2-hydroxy-5-methylisophthaldialdehyde bis(guanylhydrazone). A solution of 243 mg (2.2 mmole, 1.1 equiv/aldehyde) aminoguanidine HCl (Aldrich Chemical, Milwaukee, Wis.) in water (0.75 ml) was added to a suspension of 2-hydroxy-5-methylisophthaldialdehyde (Aldrich, 164 mg, 1 mmole) in ethanol (5 ml). After two hr at reflux the mixture was cooled. After 18 hr the crystalline solid which separated was filtered out and washed with ethanol to yield 270 mg (77%) of 2-hydroxy-5-methylisophthaldialdehyde bis(guanylhydrazone).

The activities of the compounds of the present invention are active in the following assays for biological activity: depolymerizing hemozoin, killing malaria parasites, and inhibiting the deleterious activity of hemozoin on host cells, such as macrophages. Compounds active in these tests are clinically useful for the treatment of malaria and its sequelae. These procedures and results are summarized herein and described in detail in the Examples, below.

Compounds of the present invention demonstrate activity in depolymerizing synthetic hemozoin. This activity is evaluated by incubating a suspension of monomer-free hemozoin at 37° C. with compounds of the present invention for 16 hours. After incubation, hemozoin is separated from any solubilized heme and soluble heme oligomers, the oligomers depolymerized, and the heme present in the supernatants determined.

To determine the effectiveness of the compounds of the present invention against the erythrocytic stage of the malarial parasite, P. falciparum was grown in human erythrocyte suspensions and maintained at 37° C. in candle jars according to the method of Trager and Jensen (15,16). Parasites were stage-synchronized by incubating mainly ring-stage infected erythrocytes in 5% sorbitol for 10 minutes at room temperature (17). Cultures undergo one growth cycle (2 days) before use. Strains used include the chloroquine sensitive strains D10 and HB3, and the chloroquine resistant isolates Dd2 and FCR.

Parasite growth was determined by measuring incorporation of [$^3$H]-hypoxanthine into the nucleic acids of the parasite (18). Effects of the compounds of the present invention on parasite growth was determined by measuring the reduction in incorporation of radiolabel as compared to controls. Briefly, assays are performed in 96-well microtiter plates. After 24 h of candle jar incubation at 37° C., [$^3$H]-hypoxanthine is added to each well. After 18 h the plates are harvested onto glass fiber filter 96 well plates using a cell harvester, dried, and the amount of radioactivity is determined. Drug $IC_{50}$ values (molar concentration which decreases [$^3$H]-hypoxanthine incorporation by 50% as compared to drug-free controls) are calculated by extrapolation of the log dose-response curves using curve fitting software (Origin, Microcal Software, Northampton, Mass.).

A further evaluation of compounds was performed for activity against pathophysiological effects of hemozoin on the host, using hemozoin-laden macrophages in culture. Freshly-isolated human monocytes were suspended in medium and hemozoin at a concentration reflective of the amount of hemozoin released into circulation during schizogony. In order to maximize contact between hemozoin and monocytes, the cell preparations were centrifuged for 5 sec at 150×g. Ingestion of hemozoin is essentially complete by two hours. Cells were then washed, plated and kept in a humidified incubator. The test compounds of the present invention were added to the wells at concentrations ranging from 0 to 20 mM. Macrophage viability was determined by direct microscopic examination (gross morphology and detachment from the well), trypan blue exclusion method, and LDH release. Only drug concentrations that do not induce macrophage toxicity were tested in subsequent assays. At various times post-treatment (1 hour; 3 hours), cells were lysed, extensively washed and spun down (2500× g) to pellet any cellular components including hemozoin. The lysates were then treated with alkali to dissolve hemozoin to give monomeric heme (35). Monomeric heme was quantified as described above.

Effects on macrophage functions: Arese and colleagues (30,31) have described several macrophage effector functions that are significantly suppressed and/or inhibited after ingestion of hemozoin, or plasmodium-infected red blood cells. The overall decrease in macrophage effector functions may contribute significantly to the functional immunosuppression and increased susceptibility to infections observed in malaria patients. Furthermore, Arese and colleagues have data supporting the role of the ingested hemozoin in macrophage dysfunction. Therefore, the compounds of the present invention were evaluated to assess their ability to induce recovery of macrophage effector functions induced by hemozoin. Initially, the effect of the compounds of the present invention were evaluated on spontaneous and PMA-elicited oxidative burst by freshly isolated human monocytes. As will be elaborated upon in the Examples below, freshly isolated human monocytes were plated at $5 \times 10^6$ cells/ml, and allowed to equilibrate to 37° C. for 1 h. Compounds of the instant invention were added at a final concentration of 25 uM and PMA added to 200 nM final concentration. Cell suspension aliquots were taken at 30, 60, and 120 minutes, and 14 hours. The oxidative burst was measured by luminol-elicited chemiluminescence for 30 sec., and data expressed as counts per $0.5 \times 10^6$ cells. 2-(cyclohexylimino)-1,2-dihydro-4-methyl-1-[3-(dimethylamino)propyl]naphtho-[1,2-d]thiazol-5-ol was a strong inhibitor of the oxidative burst.

In yet another aspect of the present invention, provided herein are pharmaceutical compositions of the above compounds. Such pharmaceutical compositions may be for administration by injection, or by oral, pulmonary, nasal delivery. Routes of injection include intravenous, intraarterial, intramuscular, intradermal, subcutaneous, intraperitoneal, intraventricular, and intracranial administration. In general, comprehended by the invention are pharmaceutical compositions comprising effective amounts of one or more compounds of the present invention, together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present compounds and derivatives. See, e.g., Remington's Pharmaceutical Sciences, 18th Ed. (1990, Mack Publishing Co., Easton, Pa. 18042) pages 1435–1712 which is herein incorporated by reference. The compositions may be prepared in liquid form, or may be in dried powder, such as lyophilized form.

As mentioned above, the compounds of the present invention uncharged or may be in the form of their biologically and pharmaceutically acceptable salts. Useful salt forms include but are not limited to the halides, particularly the hydrobromide, hydrochloride, dihydrochloride, sulfate, hemisulfate, dimethanesulfonate, tosylate, methanesulfonate, and mesitylenesulfonate salts. As several of the compounds described herein have multiple charges, suitable salts may include multiples or combinations of salts, such as hydrochloride and hydrobromide, and trihydrochloride. Other related salts can be formed using similarly non-toxic, and biologically and pharmaceutically acceptable anions.

Contemplated for use herein are oral solid dosage forms, which are described generally in Remington's Pharmaceutical Sciences, cited above, at Chapter 89, which is incorporated herein by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers.(e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Controlled release oral formulation may be desirable. The drug could be incorporated into an inert matrix which permits release by either diffusion or leaching mechanisms, e.g., gums. Slowly degenerating matrices may also be incorporated into the formulation. Some enteric coatings also have a delayed release effect.

For the compounds of the present invention, as further studies are conducted, information will emerge regarding appropriate dosage levels for treatment of various conditions in various patients, and the ordinary skilled worker, considering the therapeutic context, age and general health of the recipient, will be able to ascertain proper dosing. For example, a dose of 1 mg up to about 500 mg per day is embraced herein.

A subject in whom administration of a compound of the present invention is an effective therapeutic regiment for malaria is preferably a human, but can be any susceptible or infected mammal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), i.e., for veterinary medical use.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1
PREPARATION OF NAPHTHOTHIAZOLIUM SALTS OF THE PRESENT INVENTION

General Analytical Methods. All synthetic products were characterized by $^1$H NMR, $^{13}$C NMR, elemental analysis, and melting point (for solids). NMR spectra are performed on an Eclipse 400 MHZ NMR spectrometer with DELTA software (JEOL USA Inc, Peabody Mass.); alternatively, NMR spectra were obtained through Spectral Data Services, Inc. (Champaign Ill.). Elemental analyses were performed by Robertson Microlit Labs (Madison N.J.). Melting points were determined on an IA9100 digital melting point apparatus (Electrothermal Inc., Gillette N.J.).

General Synthetic Approach. The syntheses, based on the method of Lau and Gompf (29), as modified by Ulrich and Cerami (20), involve reaction of a 2-fold excess of a 1,4-quinone such as 2-methyl-1,4-naphthoquinone (menadione) with an N-substituted or an N,N'-disubstituted thiourea derivative in ethanol in the presence of 1 equiv of hydrochloric acid at room temperature in the dark, typically for 24–48 hrs. If amine functions are present in the side chain, sufficient additional hydrochloric acid is added to neutralize them. Often the crude product separates out overnight and can be filtered and recrystallized from a suitable solvent system such as ethanol-ethyl acetate. If product does not separate, from the initial reaction mixture after several days, it is concentrated and treated with ethyl acetate or ether to induce crystallization.

Many substituted thioureas are commercially available as starting materials. Others are conveniently synthesized (19) by reacting an alkyl or aryl isothiocyanate with ammonia (for monosubstituted thioureas) or a primary amine (for disubstituted thioureas) in ether or isopropanol. If solid, product does not separate out within 16 hr, the solvent is evaporated and the crude thiourea derivative is triturated with ether to induced crystallization. Thioureas so produced are of satisfactory purity for naphthothiazole synthesis without further purification.

Two illustrative syntheses of new naphthothiazolium salts, 2-(cyclohexylimino)-1,2-dihydro-4-methyl-1-[3-(dimethylamino)propyl]naphtho[1,2-d]thiazol-5-ol and 4-methyl-2-[[3-(4-morpholino)propyl]amino]naphtho[1,2-d]thiazol-5-ol, are depicted below, respectively.

In the cyclization reactions to form these naphthothiazolium derivatives from unsymmetrical thioureas, two different cyclization products are possible, in which either one or the other of the two non-equivalent thiourea nitrogens becomes the thiazole ring nitrogen. Based on NMR analysis of the products, it has been found (13, 14) that when the two thiourea substituents differ significantly in steric requirements, the least sterically demanding substituent will reside on the ring nitrogen in the isolated product. This is due to the severe steric demand caused by the proximity of H-9 to the ring-N substituent (see diagram above). Thus, by selection of the size of the other thiourea substituent, it is possible to control the position of a group of pharmacological interest, such as an aminoalkyl group, so that it resides either on the ring nitrogen (when the other group is bulky such as secondary alkyl or phenyl), or on the 2-amino nitrogen (when the other group is small such as H or methyl). This phenomenon is depicted in the following figure:

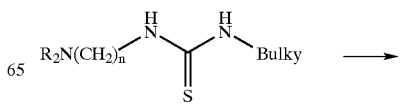

-continued

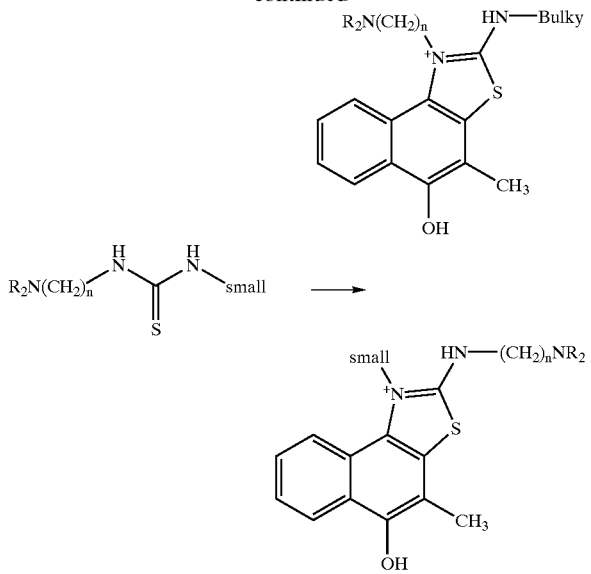

Synthesis of 1-(3-dimethylaminopropyl)-2-cyclohexylamino-5-hydroxy-4-methyl-naphtho[1,2-d]thiazolium chloride hydrochloride:

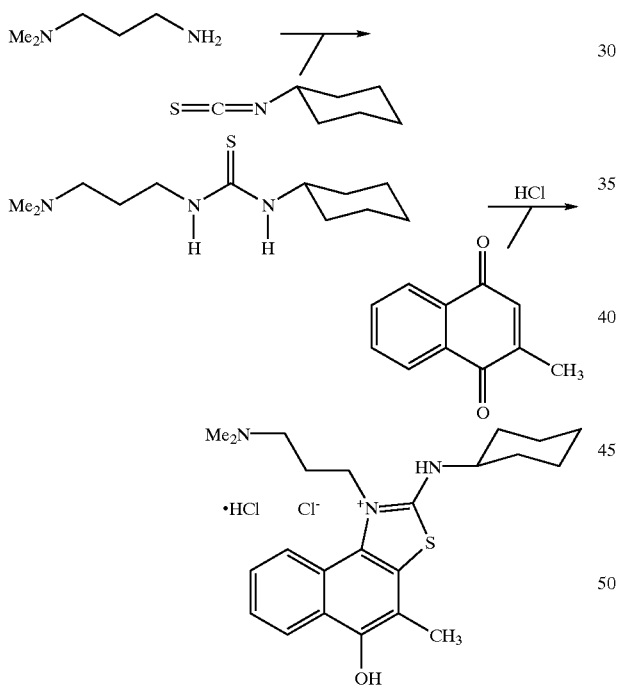

A solution of cyclohexyl isothiocyanate (5.65 g, 40 mmole) (Aldrich Chemical, Milwaukee, Wis.) in diethyl ether (15 ml) was added to a stirred solution of 3-dimethylaminopropylamine (4.2 g, 41 mmole) (Aldrich) in isopropanol (15 ml) with cooling in an ice bath. The mixture was allowed to reach room temperature and was stirred for 16 hr. The crystalline N-cyclohexyl-N'-(3-dimethylaminopropyl)thiourea which separated was filtered out and washed with ether, yielding 7.3 g (75%) white solid, melting pt. 62–67° C. A portion of this thiourea derivative (2.43 g, 10 mmole) was dissolved in ethanol (12.5 ml) containing aq. conc. HCl (1.75 ml, 20 mmole). To this stirred solution was added a hot solution of 2-methyl-1,4-naphthoquinone (3.44 g, 20 mmole) in ethanol (25 ml). The hot mixture was allowed to cool and was stored at room temperature in the dark for 2 days. The crude product which separated was filtered out and washed with ethyl acetate to yield 1.86 g (40%) of crude product. Of this, 1.5 g was recrystallized by dissolving in 20 ml hot ethanol and adding 120 ml of warm acetone; the white powder which separated on cooling was filtered out and washed with ethyl acetate to give 1.14 g (30%) of 1-(3-dimethylaminopropyl)-2-cyclohexylamino-5-hydroxy-4-methylnaphtho[1,2-d]thiazolium chloride hydrochloride, melting pt. 250–255° C. (dec.).

Synthesis of 2-(3-(4-morpholino)propylamino)-4-methyl-5-hydroxynaphtho[1,2-d]thiazolium chloride hydrochloride:

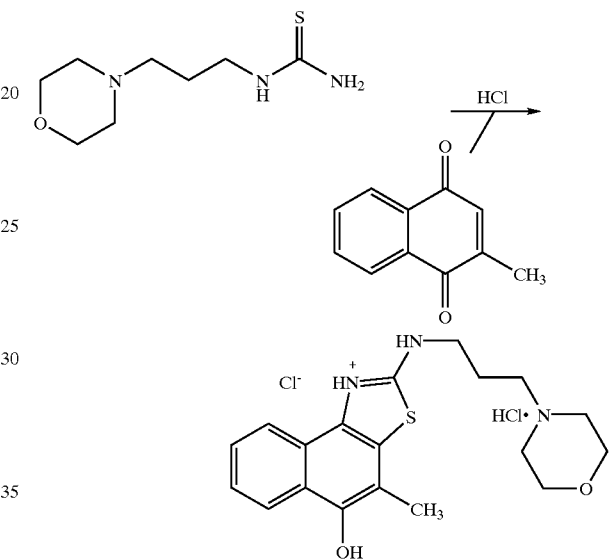

A solution of N-(3-(4-morpholino)propylamino)thiourea (Trans World Chemicals Inc., Rockville, Md., 1.016 g, 5 mmole) in ethanol (5 ml) was added to a suspension of 2-methyl-1,4-naphthoquinone (1.72 g, 10 mmole) in ethanol. The mixture was treated with conc. aq. HCl (0.83 ml, 10 mmole) and heated until the quinone dissolved. The mixture was allowed to cool and the flask was stored 3 days at room temp. in the dark. The solvent was removed in vacuo and the residue was triturated with 1:1 ethanol-ethyl acetate. The light pinkish tan powdery solid was filtered out and dried, weighing 1.479 g. Recrystallization of 1.0 g by dissolving in 50 ml hot methanol and diluting with 100 ml warm ethyl acetate gave on filtration and drying 0.883 g (63%) off-white powder, melting pt. 266–270° C. (dec.).

Synthesis of 2-[[3-[1-[2-(aminoiminomethyl)hydrazono] ethyl]phenyl]amino]-4-methylnaphtho[1,2-d]thiazol-5-ol. 3-acetylaniline (6.76 g, 50 mmole) in ethanol (50 mL) was treated with methyl isothiocyanate (3.42 mL, 50 mmole). After stirring 18 hr at room temperature, the crystalline N-(3-acetylphenyl)-N'-methylthiourea product was filtered out (7.75 g, 75% yield, mp 119–120° C.). This thiourea (3.5 g, 16.8 mmole) was combined with 2-methylnaphthoquinone (5.8 g, 33.6 mmole) in 35 mL ethanol in the presence of 12N aq. HCl (1.4 mL, 16.8 mmole). After 24 hr, filtration and washing with ethanol, ethyl acetate and ether and air drying gave 2-(3-acetylphenyl)amino-1,4-dimethyl-5-hydroxynaphtho[1,2-d]thiazolium chloride (1.62 g, 24%). This keto naphthothiazolium salt (0.80 g, 2.0 mmole) was heated at reflux in 80% methanol (12 mL) containing aminoguanidine hydrochloride (0.24 g, 2.2 mmole) for 40 hr and allowed to cool. Filtration 0.80 g off-white powder. Recrystallization of 0.75 g from methanol gave 0.42 g 2-[[3-[1-[2-(aminoiminomethyl)hydrazono]ethyl]phenyl]amino]-4-methylnaphtho[1,2-d]thiazol-5-ol as a pale yellow powder, mp 252–257° C. (dec.).

Synthesis of 8-[1-[2-(aminoiminomethyl)hydrazono]ethyl]-2-(butylimino)-1,2-dihydro-1,4-dimethylnaphtho[1,2-d]thiazol-5-ol. 6'-Methyl-2'-acetonaphthone (Aldrich Chemical Co., 5.52 g, 30 mmole) in acetic acid (22 mL) was treated dropwise with a solution of chromium trioxide (15 g, 150 mmole) in aq. 45% (v/v) acetic acid (20 mL) with stirring and cooling in a 25° C. water bath. After stirring 16 hr at room temp., the mixture was diluted with 200 mL water. The yellow solid which separated was filtered out and recrystallized from isopropanol (40 mL) to give 6-acetyl-2-methyl-1,4-naphthoquinone (2.82 g, 44%), mp 126° C. This quinone (1.284 g, 6.0 mmole) was combined with N-butyl-N'-methylthiourea (13, 14) (0.584 g, 4 mmole) in ethanol (20 mL), treated with 12N HCl (0.34 mL, 4 mmole), heated to reflux and allowed to cool. After 42 hr at room temp., filtration gave 8-acetyl-2-butylamino-1,4-dimethyl-5-hydroxynaphtho[1,2-d]thiazolium chloride (0.515 g, 34%). This keto thiazolium salt (0.284 g, 0.75 mmole) was heated at reflux with aminoguanidine HCl (0.110 g, 1 mmole) in aq. 85% ethanol (7 mL) for 44 hr. Cooling and filtration gave 8-[1-[2-(aminoiminomethyl)hydra-zono]ethyl]-2-(butylimino)-1,2-dihydro-1,4-dimethylnaphtho[1,2-d]thiazol-5-ol (0.170 g, 48%), mp 260–264° C. (dec.).

EXAMPLE 2

SYNTHESIS OF ADDITIONAL NAPHTHOTHIAZOLIUM SALTS

Following the reaction schemes described above, the following additional compounds were prepared:

| Compound | Melting point |
| --- | --- |
| 1-ethyl-2-(ethylimino)-1,2-dihydro-4-methylnaphtho[1,2-d]thiazol-5-ol monohydrochloride | 262–263° C. (dec) |
| 1,2-dihydro-1,4-dimethyl-2-[[3-(4-methyl-1-piperazinyl)propyl]imino]-naphtho[1,2-d]thiazol-5-ol trihydrochloride | 255–258° C. (dec) |
| 2-(cyclohexylimino)-1,2-dihydro-4-methyl-1-[3-(dimethylamino)propyl]-naphtho[1,2-d]thiazol-5-ol dihydrochloride | 250–255° C. (dec) |
| 2-[[3-[1-[2-(aminoiminomethyl)hydrazono]ethyl]phenyl]amino]-4-methylnaphtho[1,2-d]-thiazol-5-ol dihydrochloride | 252–257° C. (dec) |
| 2-[[3-[bis(2-hydroxyethyl)amino]propyl]imino]-1,2-dihydro-1,4-di-methylnaphtho[1,2-d]thiazol-5-ol dihydrochloride | 268–270° C. (dec) |
| 1,2-dihydro-4-methyl-1-(2-propenyl)-2-(2-propenylimino)naphtho[1,2-d]thiazol-5-ol monohydrochloride | 229–230° C. (dec) |
| 4-methyl-2-(2-propenylamino)naphtho[1,2-d]thiazol-5-ol monohydrochloride | 240–245° C. (dec) |
| 2-(cyclohexylimino)-5-hydroxy-4-methylnaphtho[1,2-d]thiazole-1(2H)-ethanol monohydrochloride | 196–197° C. (dec) |
| 1,2-dihydro-2-[(2-hydroxyethyl)imino]-1,4-dimethyl-naphtho[1,2-d]thiazol-5-ol monohydrochloride | 233–234° C. (dec) |
| 1,2-dihydro-1,4-dimethyl-2-(phenylimino)naphtho[1,2-d]thiazol-5-ol monohydrochloride | 258–266° C. (dec) |
| 1,2-dihydro-4-methyl-2-(phenylimino)naphtho[1,2-d]thiazol-5-ol monohydrochloride | 263–264° C. (dec) |
| 4-methyl-2-[[3-(4-morpholino)propyl]amino]naphtho[1,2-d]thiazol-5-ol dihydrochloride | 266–270° C. (dec) |
| 8-[1-[2-(aminoiminomethyl)hydrazono]ethyl]-2-(butylimino)-1,2-dihydro-1,4-dimethylnaphtho[1,2-d]thiazol-5-ol monohydrochloride | 260–264° C. (dec) |

EXAMPLE 3

SYNTHESIS OF AROMATIC GUANYLHYDRAZONES

The following aromatic monoguanylhydrazones were prepared.

Synthesis of 5-(1-[2-(aminoiminomethyl)hydrazono]ethyl)salicylic acid hydrochloride. 5-Acetylsalicylic acid (3.6 g) and aminoguanidine hydrochloride (2.4 g) were heated in 80% ethanol (25 mL) for 2 hr. Cooling and filtration gave 5.2 g of crude 5-(1-[2-(aminoiminomethyl)hydrazono]ethyl)salicylic acid hydrochloride. Of this, 0.58 g was purified by dissolving in aq. NaOH (pH 12.5) and reprecipitation with aq HCl (to pH 2) to give 0.45 g of 5-(1-[2-(aminoiminomethyl)hydrazono]ethyl)salicylic acid hydrochloride, mp 312–3° C. (dec).

Synthesis of 2[(3,4-dihydroxyphenyl)ethylidyne]hydrazinecarboximidamide hydrochloride. 3,4-dihydroxyacetophenone (3.04 g) and aminoguanidine hydrochloride (2.44 g) were heated in 75% ethanol (16 mL) for 4 hr under nitrogen. Cooling and filtration gave 2.7 g of 2-[(3,4-dihydroxyphenyl)ethylidyne]hydrazinecarboximidamide hydrochloride, mp 242–5° C.

Following the above procedures, the following compounds were prepared:

| Compound | Melting point |
| --- | --- |
| 2-[(2,3-dihydroxyphenyl)methylene]hydrazinecarboximidamide hydrochloride | 205–208° C. |
| 2-[(2-hydroxyphenyl)methylene]hydrazinecarboximidamide hydrochloride | 222–223° C |
| 2-[(2-hydroxy-5-methoxyphenyl)methylene]hydrazine-carboximidamide hydrochloride | 209–212° C. (dec) |
| 2-[(2-hydroxy-1-naphthyl)methylene]hydrazine-carboximidamide monohydrochloride | 226–228° C. (dec) |
| 2-[(1-hydroxy-2-naphthyl)ethylidene]hydrazine-carboximidamide hydrochloride | 284–286° C. (dec) |
| 2-[(2-pyridyl)methylene]hydrazinecarboximidamide hemisulfate | 246–248° C. (dec) |
| 2-[(4-quinolinyl)methylene]hydrazinecarboximidamide hydrochloride | 273–275° C. (dec) |
| 2-[(3,4-dihydroxyphenyl)ethylidene]hydrazine-carboximidamide hydrochloride | 242–244° C. (dec) |
| 2-[(4-hydroxyphenyl)ethylidene]hydrazinecarboximidamide hydrochloride | 257–260° C. (dec) |
| 2-[(2-hydroxyphenyl)ethylidene]hydrazinecarboximidamide hydrochloride | 236–240° C. (dec) |
| 2-[(2-hydroxy-4-methoxyphenyl)methylene]hydrazine-carboximidamide hydrochloride | 205–207° C. |
| 2-{[2-hydroxy-4-(diethylamino)phenyl]methylene}hydrazinecarboximidamide | 250–255° C. (dec) |
| 2-[[3-(3,4-dimethyl-2(3H)-imino-6-pyrimidinyl)phenyl]ethylidene]hydrazinecarboximidamide hydrochloride hydroiodide | 315–318° C. (dec) |
| 2-[[4-(3,4-dimethyl-2(3H)-imino-6- | 302–305° C. |

-continued

| Compound | Melting point |
|---|---|
| pyrimidinyl)phenyl]ethylidene]hydrazinecarboximidamide hydrochloride hydroiodide | (dec) |
| 2-[1-(4-benzyloxy-2-hydroxy-3-methylphenyl)ethylidene]hydrazinecarboximidamide hydrochloride | 251–253° C. (dec) |
| 2-amino-3-[(aminoiminomethyl)hydrazono]methyl]-6-chloro-4H-1-benzopyran-4-one hydrochloride | 330–331° C. (dec) |
| 2-[(1,4-dihydro-1,4-dioxo-3-methyl-7-naphthalenyl)ethylidene]hydrazinecarboximidamide hydrochloride | 308–312° C. (chars) |
| 2-[[1-[(aminoiminomethyl)hydrazono]-1,4-dihydro-3-methyl-4-oxo-7-naphthalenyl]ethylidene]hydrazinecarboximidamide hydrochloride | 270–275° C. (chars) |

The following aromatic bis(guanylhydrazones) were prepared: 2-Hydroxy-5-methylisophthaldialdehyde bis (guanylhydrazone): A solution of 243 mg (2.2 mmole, 1.1 equiv/aldehyde) aminoguanidine HCl (Aldrich Chemical, Milwaukee, Wis.) in water (0.75 ml) was added to a suspension of 2-hydroxy-5-methylisophthaldialdehyde (Aldrich, 164 mg, 1 mmole) in ethanol (5 ml). After two hr at reflux the mixture was cooled. After 18 hr the crystalline solid which separated was filtered out and washed with ethanol to yield 270 mg (77%) of 2-hydroxy-5-methylisophthaldialdehyde bis(guanylhydrazone), melting pt. 204–206° C. (dec).

2,6-diacetylpyridine bis(dimethylaminoacetylhydrazone) dihydrochloride: A solution of 2,6-diacetylpyridine (Aldrich Chemical, Milwaukee, Wis., 0.815 g, 5 mmole) in hot ethanol (10 ml) was mixed with a solution of dimethylaminoacethydrazide hydrochloride (Avocado/Alfa Aesar, Ward Hill, Mass.) in warm water (10 ml). The mixture was heated to reflux briefly and allowed to cool. After 3 hrs the mixture was diluted with 20 ml isopropanol, causing a copious precipitate to form. The precipitate was filtered out and washed with isopropanol. Drying gave 2.065 g (95%) white crystalline solid, melting pt. 280–282° C. (dec.).

Following similar procedures, the following compounds were prepared:

| Compound | Melting point |
|---|---|
| 2,2'-[(4,6-dihydroxy-1,3-phenylene)diethylidyne]bis(hydrazinecarboximidamide) dihydrochloride | 335–337° C. (dec) |
| 2,2'-[(4-hydroxy-1,3-phenylene)diethylidyne]bis(hydrazinecarboximidamide) dihydrochloride | 318–319° C. (dec) |
| 2,2'-(1,3-phenylenediethylidyne)bis(hydrazinecarboximidamide) dihydrochloride | 330–333° C. (dec) |
| 2,2'-[(2-hydroxy-5-methyl-1,3-phenylene)dimethylidyne]bis(hydrazinecarboximidamide) | 204–206° C. (dec) |
| 2,2'-[(2-methoxy-5-methyl-1,3-phenylene)dimethylidyne]bis(hydrazinecarboximidamide) dihydrochloride | 298–300° C. (dec) |
| 2,2'-[(2-amino-1,3-phenylene)diethylidyne]bis(hydrazinecarboximidamide) dihydrochloride | 335–338° C. (dec) |
| 2,2'-[(4-hydroxy-1,3-phenylene)dimethylidyne]bis(hydrazinecarboximidamide) dihydrochloride | 200–202° C. (dec) |
| 2,2'-(1,3-phenylenedimethylidyne)bis(hydrazinecarboximidamide) dihydrochloride | 279–282° C. |
| 2,2'-(2,6-pyridinediyldiethylidyne)bis(hydrazinecarboximidamide) dihydrochloride | 350–370° C. (chars) |
| 2,2'-(3,5-pyridinediyldiethylidyne)bis(hydrazinecarboximidamide) dihydrochloride | 360–370° C. (dec) |
| 2,2'-[(2,6-dimethyl-3,5-pyridinediyl)diethylidyne]bis(hydrazinecarboximidamide) dimethanesulfonate | 188–189° C. (dec) |
| 2,6-bis[1-[[(dimethylamino)acetyl]hydrazono]ethyl]pyridine dihydrochloride | 281–283° C. (dec) |
| 2,2'-[(5-amino-1,3-phenylene)diethylidyne]bis(hydrazinecarboximidamide) dihydrochloride | 355–360° C. (dec) |
| 2,2'-[(5-hydroxy-1,3-phenylene)diethylidyne]bis(hydrazinecarboximidamide) dihydrochloride | 330–337° C. (dec) |

EXAMPLE 4

ASSAY FOR DEPOLYMERIZATION OF SYNTHETIC HEMOZOIN

The synthesis of synthetic hemozoin is carried out as previously described (26). In brief, 60 μmoles of hematin was dissolved in 8 ml of 0.1N NaOH. Following dissolution 49 mmoles of glacial acetic acid was added and the suspension heated at 70° C. overnight. The precipitate was then washed extensively with LPS-free water. In order to remove unreacted heme the precipitate was extracted with 0.1M sodium bicarbonate (pH 9.1) for three hours. The remaining insoluble material was recovered by centrifugation, resuspended in EtOH and transferred to sterile Eppendorf tubes. The material was washed several times in EtOH and finally resuspended in LPS-free double-distilled $H_2O$. The hemozoin preparation was then tested for endotoxin by using the Limulus Amebocyte Lysate test following manufacturer's instructions. Although the preparation of LPS-free hemozoin from native or synthetic sources is not critical for in vitro depolymerization studies, it is critical for studies involving monocytes and animals (see Examples below). Small amounts of LPS can evoke a considerable cytokine response and interfere with interpretation of results. The amount of heme in the final product was determined from a small aliquot using the pyridine-hemochrome method as previously described (26). The preparations are stored at 4° C. until used. This method routinely converts 40–50% of the starting material into polymer. This material is chemically identical to purified native hemozoin as assessed by infrared and X-ray absorption spectroscopic analysis.

A suspension of monomer-free hemozoin (equivalent to 2 mM free heme) as prepared above was incubated at 37° C. with 50 mM test compound in total volume of 500 μl in acetate buffer (pH: 5.0) in siliconized Eppendorf tubes (Brinkmann Instruments, Westbury, N.Y.) for 16 hours. A control sample containing distilled $H_2O$ instead of hemozoin was included. The samples were centrifuged at 14,000 rpm (Eppendorf centrifuge model 5415C, Brinkmann Instruments, Westbury, N.Y.) for 20 min; then 225 μl supernatant was diluted in 175 μl acetate buffer (pH 5.0). Another 225 μl was added to 175 μl 0.5 M NaOH to dissolve possible oligomeric depolymerization products to monomers. Half of the pellet was washed twice for 2.5 hr in 200 μl 2.5% SDS (v/v) in $dH_2O$, the other half was washed twice in 200 μl $HCO_3^-$ buffer (pH: 9.1). Both sample supernatants and SDS and $HCO_3^-$ buffer supernatants were centrifuged 14,000 rpm for 20 min. and supernatants were added to 10 μl sodium dithionite (200 mg/ml $dH_2O$) to reduce the heme monomers in solution to $Fe^{2+}$. All samples were measured in triplicate at 540 nm (Model UV1601 spectrophotometer, Shimradzu Corp, Columbia, Md.). The OD obtained from the blind sample was subtracted from the OD of the hemozoin containing sample. The results, together with that of effects on parasite growth, are shown hereinbelow in Tables 1–4.

EXAMPLE 5

EVALUATION OF COMPOUNDS FOR ACTIVITY AGAINST THE ERYTHROCYTIC STAGE OF THE MALARIAL PARASITE

Parasites were grown in A$^+$ human erythrocyte suspensions using RPMI-1640 (GIBCO, Gaithersburg, Md.) medium supplemented by 25 mM HEPES (pH 7.35), 0.2% NaHCO$_3$ (23 mM), 0.2% (D)-Glucose and 10% human A$^+$ plasma and maintained at 37° C. in candle jars according to the method of Trager and Jensen (20,21) Parasites are stage synchronized by incubating mainly ring-stage infected erythrocytes in 5% sorbitol for 10 minutes at room temperature (22). Cultures undergo one growth cycle (2 days) before use. Strains used include the chloroquine sensitive strains D10 and HB3, and the chloroquine resistant isolates Dd2 and FCR.

Parasite growth was determined by measuring incorporation of [$^3$H]-hypoxanthine into the nucleic acids of the parasite as previously described (23). Effects of the compounds of the present invention on parasite growth was determined by measuring the reduction in incorporation of radiolabel as compared to controls. Briefly, assays were performed in 96-well microtiter plates, each well containing 200 μl of synchronized ring-stage infected erythrocytes in complete media and 50 μl of drug dilution or solvent. The final hematocrit was 1.5% and percent parasitemias range from 2–8%. After 24 h of candle jar incubation at 37° C., 2.5 μCi of [$^3$H]-hypoxanthine (17 Ci/mmol, Amersham, Arlington Heights, Ill.) in RPMI-1640 media supplemented with 25 mM HEPES (pH 7.35), 0.2% NaHCO$_3$ (23 mM), 0.2% (D)-Glucose is added to each well. After 18 h the plates were harvested onto glass fiber filter 96 well plates using a cell harvester, dried, and 25 μl scintillation acid added per well. The, amount of radioactivity was determined. Drug IC$_{50}$ values (molar concentration which decreases [$^3$H]-hypoxanthine incorporation by 50% as compared to drug-free controls) are calculated by extrapolation of the log dose-response curves using curve fitting software (Origin, Microcal Software, Northampton, Mass.). The effects on parasite grown by aromatic guanyllhydrazones, bisguanylhydrazones, naphthothiazolium salts, and other compounds of the instant invention, together with data on hemozoin depolymerization from Example 5, are shown in tables 1 through 4, respectively.

TABLE 1

Activity of aryl monoguanylhydrazones on *P. falciparum* growth in culture and on depolymerization of synthetic hemozoin in vitro

| Structure | Compound | IC50 vs. P. falc. | % depol. hemoz. |
|---|---|---|---|
| (structure: H$_2$N-C(=NH·HCl)-NH-N=CH-phenyl-2,3-(OH)$_2$) | 2-[(2,3-dihydroxyphenyl)methylene]hydrazinecarboximidamide hydrochloride | >10 μM | 4.1% |
| (structure: H$_2$N-C(=NH·HCl)-NH-N=CH-phenyl-2-OH) | 2-[(2-hydroxyphenyl)methylene]hydrazine carboximidamide hydrochloride | 3.5 μM | 3.5% |
| (structure: H$_2$N-C(=NH·HCl)-NH-N=CH-phenyl-2-OH-5-OCH$_3$) | 2-[(2-hydroxy-5-methoxyphenyl)methylene]hydrazine-carboximidamide hydrochloride | 4.4 μM | 0.9% |
| (structure: 2-hydroxy-1-naphthyl-CH=N-NH-C(=NH·HCl)-NH$_2$) | 2-[(2-hydroxy-1-naphthyl)methylidene]hydrazine-carboximidamide monohydrochloride | 1.8 μM | 4.3% |

TABLE 1-continued

Activity of aryl monoguanylhydrazones on *P. falciparum* growth in culture and on depolymerization of synthetic hemozoin in vitro

| Structure | Compound | IC50 vs. P. falc. | % depol. hemoz. |
|---|---|---|---|
| (structure) | 2-[(1-hydroxy-2-naphthyl)ethylidene]hydrazine-carboximidamide hydrochloride | 6 μM | ND |
| (structure) | 2-[(4-quinolinyl)methylene]hydrazine-carboximidamide hydrochloride | 3.4 μM | ND |
| (structure) | 2-[(3,4-dihydroxyphenyl)ethylidene]-hydrazinecarboximidamide hydrochloride | >10 μM | 0.5% |
| (structure) | 2-[(2-hydroxyphenyl)ethylidene]hydrazine-carboximidamide hydrochloride | >>10 μM | 0.4% |
| (structure) | 2-[(2-hydroxy-4-methoxyphenyl)methylene]hydrazine-carboximidamide hydrochloride | 1.0 μM | ND |
| (structure) | 2-[[3-(3,4-dimethyl-2(3H)-imino-6-pyrimidinyl)phenyl]ethylidene]hydrazine-carboximidamide hydrochloride hydroiodide | 1.05 uM | ND |
| (structure) | 2-[[4-(3,4-dimethyl-2(3H)-imino-6-pyrimidinyl)phenyl]ethylidene]hydrazine-carboximidamide hydrochloride hydroiodide | 0.60 uM | ND |
| (structure) | 2-[1-(4-benzyloxy-2-hydroxy-3-methylphenyl)ethylidene]hydrazine-carboximidamide hydrochloride | 1.33 uM | 1.9% |

TABLE 1-continued

Activity of aryl monoguanylhydrazones on *P. falciparum* growth in culture and on depolymerization of synthetic hemozoin in vitro

| Structure | Compound | IC50 vs. P. falc. | % depol. hemoz. |
|---|---|---|---|
| 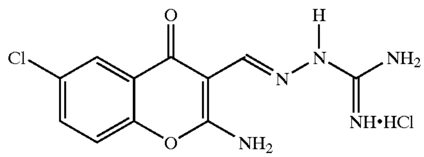 | 2-amino-3-[(aminoiminomethyl)hydrazono]methyl]-6-chloro-4H-1-benzopyran-4-one hydrochloride | 3.25 uM | 0.6% |
| 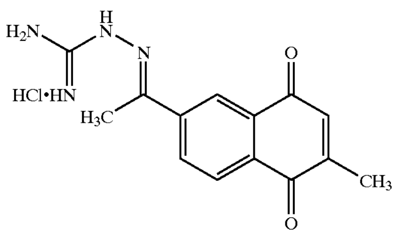 | 2-[(1,4-dihydro-1,4-dioxo-3-methyl-7-naphthalenyl)ethylidene]hydrazinecarboximidamide hydrochloride | 1.8 uM | 0.4% |
| | 2-[[1-[(aminoiminomethyl)hydrazono]-1,4-dihydro-3-methyl-4-oxo-7-naphthalenyl]ethylidene]hydrazine-carboximidamide hydrochloride | 1.7 uM | 5.1% |

ND = not determined

TABLE 2

Activity of aromatic bisguanylhydrazones on *P. falciparum* growth in culture and on depolymerization of synthetic hemozoin in vitro

| Structure | Compound | IC50 vs. P. falc. | % depol. hemoz. |
|---|---|---|---|
| 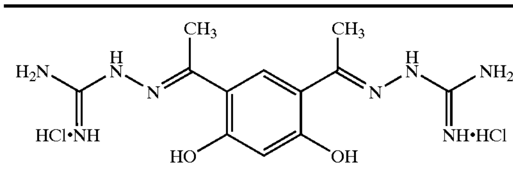 | 2,2'-[(4,6-dihydroxy-1,3-phenylene)diethylidyne]bis(hydrazinecarboximidamide) dihydrochloride | 7 μM | 2.6% |
| 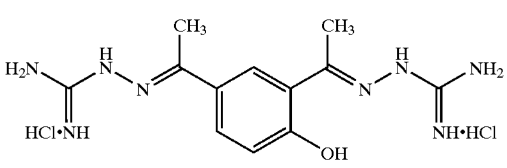 | 2,2'-[(4-hydroxy-1,3-phenylene)diethylidyne]bis(hydrazinecarboximidamide) dihydrochloride | 2.6 μM | 0.6% |
| 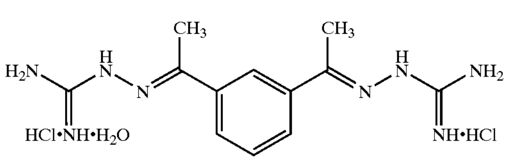 | 2,2'-(1,3-phenylenediethylidyne)bis(hydrazinecarboximidamide) dihydrochloride | 0.83 μM | 0.4% |

TABLE 2-continued

Activity of aromatic bisguanylhydrazones on *P. falciparum* growth in culture and on depolymerization of synthetic hemozoin in vitro

| Structure | Compound | IC50 vs. P. falc. | % depol. hemoz. |
|---|---|---|---|
| 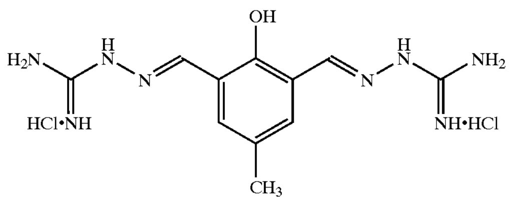 | 2,2'-[(2-hydroxy-5-methyl-1,3-phenylene)dimethylidyne]bis-(hydrazinecarboximidamide) | 0.20 μM | 2.3% |
| 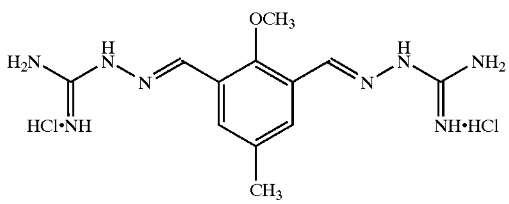 | 2,2'-[(2-methoxy-5-methyl-1,3-phenylene)dimethylidyne]bis-(hydrazinecarboximidamide) dihydrochloride | 2.3 μM | 2.0% |
| 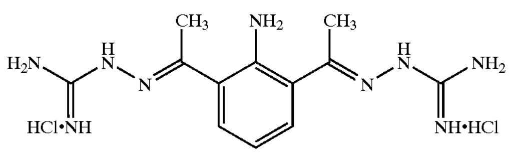 | 2,2'-[(2-amino-1,3-phenylene)diethylidyne]bis(hydrazinecarboximidamide) dihydrochloride | 6.3 μM | ND |
| 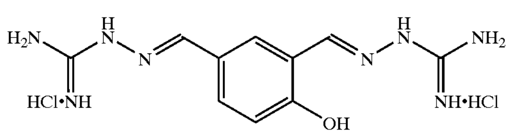 | 2,2'-[(4-hydroxy-1,3-phenylene)dimethylidyne]bis(hydrazinecarboximidamide) dihydrochloride | 5.5 μM | 2.2% |
| 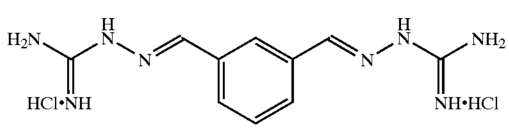 | 2,2'-(1,3-phenylenedimethylidyne)bis(hydrazinecarboximidamide) dihydrochloride | 1 μM | 0.1% |
| 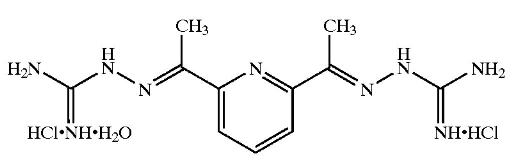 | 2,2'-(2,6-pyridinediyldiethylidyne)bis(hydrazinecarboximidamide) dihydrochloride | 2 μM | 0.0% |
| 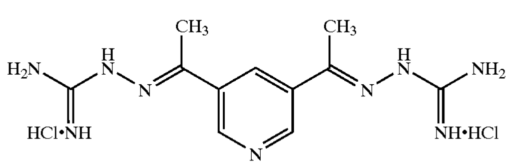 | 2,2'-(3,5-pyridinediyldiethylidyne)bis(hydrazinecarboximidamide) dihydrochloride | 0.4 μM | 0.3% |
| 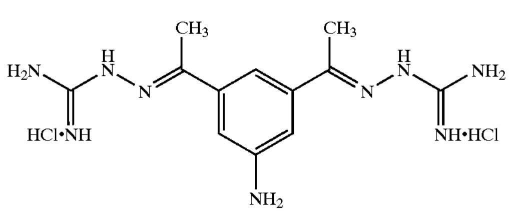 | 2,2'-[(5-amino-1,3-phenylene)diethylidyne]bis(hydrazinecarboximidamide) dihydrochloride | 4 μM | 0.3% |

TABLE 2-continued

Activity of aromatic bisguanylhydrazones on *P. falciparum* growth in culture and on depolymerization of synthetic hemozoin in vitro

| Structure | Compound | IC50 vs. P. falc. | % depol. hemoz. |
|---|---|---|---|
| (structure shown) | 2,2'-[(5-hydroxy-1,3-phenylene)diethylidyne]bis(hydrazinecarboximidamide) dihydrochloride | 1.4 μM | 0.0% |

TABLE 3

Activity of Substituted Naphthothiazolium Salts vs. *P. falciparum* in Culture and in Depolymerization of Synthetic Hemozoin in vitro
(CQR = chloroquine resistant strain)

| Structure | Compound | IC50 vs. P. falc. | % depol. hemoz. |
|---|---|---|---|
| (structure shown) | 1-ethyl-2-(ethylimino)-1,2-dihydro-4-methyl-naphtho[1,2-d]thiazol-5-ol monohydrochloride | 2.5 μM | 2.4% |
| (structure shown) | 1,2-dihydro-1,4-dimethyl-2-[[3-(4-methyl-1-piperazinyl)propyl]imino]naphtho[1,2-d]-thiazol-5-ol trihydrochloride | .075 μM (0.5 μM in CQR) | 2.0% |
| (structure shown) | 2-(cyclohexylimino)-1,2-dihydro-4-methyl-1-[3-(dimethylamino)propyl]naphtho-[1,2-d]thiazol-5-ol dihydrochloride | .075 μM (0.075 μM in CQR) | 2.2% |
| (structure shown) | 2-[[3-[1-[2-(aminoiminomethyl)hydrazono]ethyl]phenyl]-amino]-4-methylnaphthol[1,2-d]thiazol-5-ol dihydrochloride | 0.83 μM | 0.6% |

TABLE 3-continued

Activity of Substituted Naphthothiazolium Salts vs. *P. falciparum* in Culture and in Depolymerization of Synthetic Hemozoin in vitro (CQR = chloroquine resistant strain)

| Structure | Compound | IC50 vs. P. falc. | % depol. hemoz. |
|---|---|---|---|
| (structure) | 2-[[3-[bis(2-hydroxyethyl)amino]propyl]imino]-1,2-dihydro-1,4-dimethylnaphtho[1,2-d]-thiazol-5-ol dihydrochloride | 0.2 μM | 2.9% |
| (structure) | 1,2-dihydro-4-methyl-1-(2-propenyl)-2-(2-propenylimino)naphtho[1,2-d]thiazol-5-ol monohydrochloride | 6.0 μM | 4.8% |
| (structure) | 4-methyl-2-(2-propenylamino)naphtho[1,2-d]-thiazol-5-ol monohydrochloride | 6.3 μM | 0.4% |
| (structure) | 2-(cyclohexylimino)-5-hydroxy-4-methyl-naphtho[1,2-d]thiazole-1(2H)-ethanol monohydrochloride | 1.0 μM | 0.4% |
| (structure) | 1,2-dihydro-2-[(2-hydroxyethyl)imino]-1,4-dimethylnaphtho[1,2-d]thiazol-5-ol monohydrochloride | 1.4 μM | 3.1% |

TABLE 3-continued

*Activity of Substituted Naphthothiazolium Salts vs. P. falciparum in Culture and in Depolymerization of Synthetic Hemozoin in vitro*

(CQR = chloroquine resistant strain)

| Structure | Compound | IC50 vs. P. falc. | % depol. hemoz. |
|---|---|---|---|
| 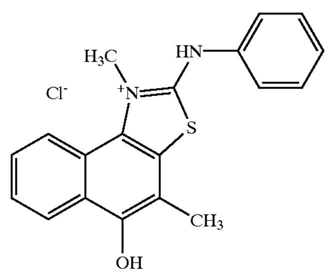 | 1,2-dihydro-1,4-dimethyl-2-(phenylimino)-naphtho[1,2-d]thiazol-5-ol monohydrochloride | >10 μM | 0.0% |
| 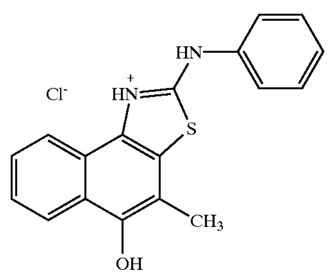 | 1,2-dihydro-4-methyl-2-(phenylimino)naphtho-[1,2-d]thiazol-5-ol monohydrochloride | 4.2 μM | 0.0% |
| 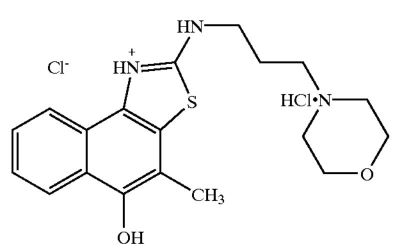 | 4-methyl-2-[[3-(4-morpholino)propylamine]-naphtho[1,2-d]thiazol-5-ol dihydrochloride | 0.6 μM | 1.1% |
| 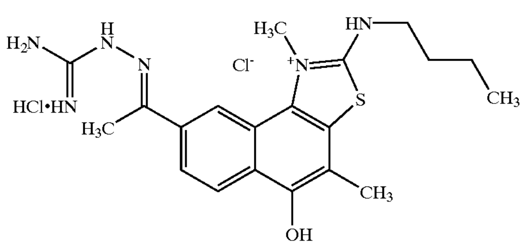 | 8-[1-[2-(aminoiminomethyl)hydrazono]ethyl]-2-(butylimino)-1,2-dihydro-1,4-dimethylnaphtho[1,2-d]thiazol-5-ol monohydrochloride | 0.6 μM | ND |

TABLE 4

Activity of compounds of the present invention vs. *P. falciparum* in Culture and in Depolymerization of Synthetic Hemozoin in vitro

| Structure | Compound | IC50 vs. P. falc. | % depol. hemoz. |
|---|---|---|---|
| 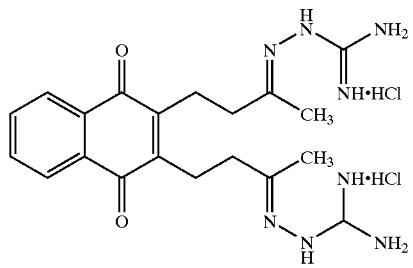 | 2,2'-[(1,4-dihydro-1,4-dioxo-2,3-naphthalenediyl)bis(1-methyl-3-propanyl-1-ylidene)]bis(hydrazinecarboximidamide)dihydrochloride | 0.8 μM | 0.3% |
| 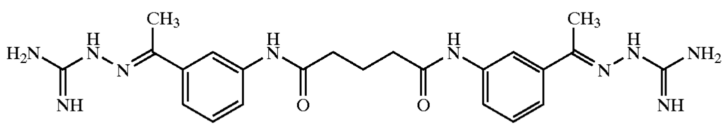 | N,N'-bis[3-[1-[(aminoiminomethyl)hydrazono]ethyl]phenyl]pentanediamide dihydrochloride | 0.8 μM | 0 |
| 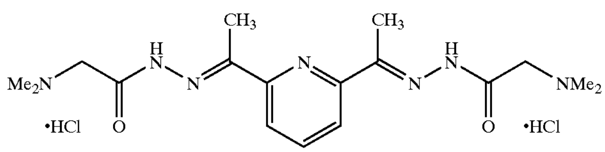 | 2,6-bis[1-[[(dimethylamino)acetyl]hydrazono]ethyl]-pyridine dihydrochloride | 1.5 μM | 0 |
| 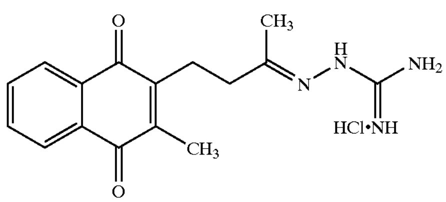 | 2-[3-(1,4-dihydro-1,4-dioxo-3-methyl-2-naphthalenyl)-1-methylpropylidene]hydrazinecarboximidamide hydrochloride | 1.3 μM | 0.1% |
| 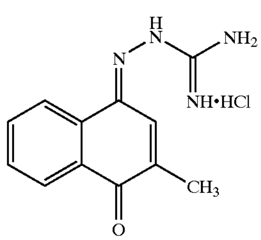 | 1-[(aminoiminomethyl)hydrazono]-1,4-dihydro-3-methyl-4-oxonaphthalene hydrochloride | 24% at 5 μM | 6.3% |
| 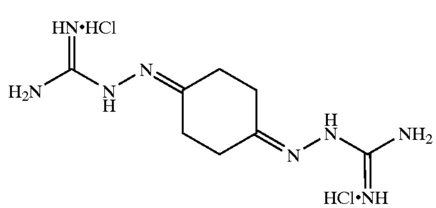 | 2,2'-(1,4-cyclohexanediylidene)bis(hydrazinecarboximidamide) dihydrochloride | 2 μM | 0 |
| 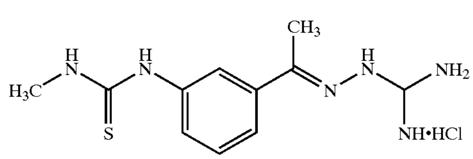 | N-[3-[1-[(aminoiminomethyl)hydrazono]ethyl]-phenyl]-N'-methylthiourea hydrochloride | ND | 2.9% |

EXAMPLE 6

ASSESSMENT OF BREAKDOWN OF MACROPHAGE-INGESTED HEMOZOIN

Human monocytes were freshly isolated from a buffy coat from a normal donor using Percoll gradients. Monocytes were plated at $5 \times 10^6$ cells per ml, and allowed to phagocytose hemozoin for 1 hour. Cells were washed thoroughly, and treated with 25 μM of compounds of the present invention. Cells were solubilized at various time points and hemozoin content determined by luminol-elicited chemiluminescence. As shown in FIG. 1, 2-(cyclohexylimino)-1,2-dihydro-4-methyl-1-[3-(dimethylamino)propyl]naphtho-[1,2-d]thiazol-5-ol dihydrochloride demonstrates hemozoin-dissolving ability. 2,2'-[(2-Hydroxy-5-methyl-1,3-phenylene)dimethylidyne]bis(hydrazinecarboximidamide) showed a significant reduction of hemozoin.

EXAMPLE 7

DOSAGE FORM

The compounds of the present invention can be formulated for oral pharmaceutical administration to a patient in need of antimalarial treatment as follows:

| Tablet | mg/tablet |
|---|---|
| Compound of the present invention | 50 |
| Starch | 50 |
| Mannitol | 75 |
| Magnesium Stearate | 2 |
| Stearic Acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearicacid and the balance of the starch are added and the entire mix blended prior to compression on a suitable tablet press. The tablets are compressed at a weight of 232 mg. using a $^{11}/_{32}$" punch with a hardness of 4 kg. These tablets will disintegrate within a half hour according to the method described in USP XVI.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

1. World malaria situation in 1994 Part I. (1997) *Wkly Epidemiol Rec*:72, 269–274.
2. Barat L M, Bloland P B. Drug resistance among malaria and other parasites. (1997) *Infect Dis Clin North Am*: 11(4), 969–987.
3. McGregor A, Barr M. Antibody response to tetanus toxoid inoculation in malarious and non-malarious Gambian children. (1962) *Trans R Soc Trop Med Hyg*:56, 364–367.
4. Bradley-Moore A M, Greenwood B M, Bradley A K. Malaria chemoprophylaxis with chloroquine in young Nigerian children. II. Effect on the immune response to vaccination. (1985) *Ann Trop Med Parasitol* :79, 563–573.
5. Ho M, Webster H K, Looareesuwan S. Antigen-specific immunosuppression in human malaria due to *Plasmodium falciparum*. (1986) *J Infect Dis*:153, 763–771.
6. Rudzinska M A, Trager W. Bray R S. Pinocytotic uptake and the digestion of hemoglobin in malaria parasites. (1965) *J Protozool*: 12(4), 563–576.
7. Schwarzer E, Turrini F, Ulliers D, Giribaldi G, Ginsburg H, Arese P. Impairment of macrophage functions after ingestion of *Plasmodium falciparum*-infected erythrocytes or isolated malarial pigment. (1992) *J. Exp. Med*:176, 1033–1041.
8. Fiori P L, Rappelli P, Mirkarimi S N, Ginsburg H, Capuccinelli P, Turrihi F. Reduced microbicidal and antitumour activities of human monocytes after ingestion of *Plasmodium falciparum*-infected red blood cells. (1993) *Parasite Immunology*: 15, 647–655.
9. Turrini F, Schwarzer E, Arese P. The involvement of hemozoin toxicity in depression of cellular immunity. (1993) *Parasitology Today*:9(8), 297–300.
10. Bohle D S, Conklin B J, Cox D, Madsen S K, Paulson S, Stephens P W, Yee G T. Structural and microscopic studies of β-hematin (the heme coordination polymer in malaria pigment). (1994) *ACS Symp. Ser.* 572 (*Inorganic and Organometallic Polymers II*), 497–515.
11. Bohle D S, Dinnebier R E, Madsen S K, Stephens P W. Characterization of the products of the heme detoxification pathway in malarial late trophozoites by x-ray diffraction. (1997) *J. Biol. Chem*:272, 713–716.
12. Chou A C, Fitch C D. Heme polymerase: modulation by chloroquine treatment of a rodent malaria. (1992) *Life Sciences*:51, 2073–2078.
13. Ulrich P C, Grady R W, Cerami A (1982) The trypanocidal activity of various aromatic bisguanylhydrazones in vivo. Drug Devel. Res. 2: 219–228
14. Ulrich P, Cerami A (1984) Trypanocidal 1,3-arylene diketone bis(guanyl-hydrazone)s. Structure-activity relationships among substituted and heterocyclic analogues. J. Med. Chem. 27: 35–40
15. Trager W, Jensen J B. Human malaria parasites in continuous culture. (1976) *Science*: 193, 673–675.
16. Jensen J B, Trager W. *Plasmodium falciparum* in culture: Use of outdated erthrocytes and description of the candle jar method. (1977) *J. Parasitol*:63, 883–886.
17. Lambros C, Vanderberg J P. Synchronization of *Plasmodium falciparum* erythrocytic stages in culture. (1979) *J. Parasitol*:65; 418–20.
18. Desjardins R E, Canfield C J, Haynes J D, Chulay J D. Quantitative assessment of antimalarial activity in vitro by a semiautomated microdilution technique. (1979) *Antimicrob. Agents Chemother*:16, 710–8.
19. Ulrich P, Cerami A, Potential antitrypanosomal agents. $1,N^2$-Disubstituted 2-amino-5-hydroxy-4-methylnaphtho [1,2-d]thiazolium salts and related compounds. (1982) *J. Med. Chem*:25, 654–657.
20. Trager W, Jensen J B. Human malaria parasites in continuous culture. (1976) *Science*: 193, 673–675.
21. Jensen J B, Trager W. *Plasmodium falciparum* in culture: Use of outdated erthrocytes and description of the candle jar method. (1977) *J. Parasitol*:63, 883–886.
22. Lambros C, Vanderberg J P. Synchronization of *Plasmodium falciparum* erythrocytic stages in culture. (1979) *J. Parasitol*:65, 418–20.
23. Desjardins R E, Canfield C J, Haynes J D, Chulay J D. Quantitative assessment of antimalarial activity in vitro by a semiautomated microdilution technique. (1979) *Antimicrob. Agents Chemother*: 16, 710–8.
24. Sherry B A, Alava G., Tracey K J, Martiney J, Cerami A, Slater A F G. (1995) Malaria-specific metabolite hemozoin mediates the release of several potent endogenous pyrogens (TNF, MIP-1α and MIP-1β) in vitro, and altered thermoregulation in vivo. *J Inflammation* 45:85–96.
26. Slater A F G, Swiggard W J, Orton B R, Flitter W D, Goldberg D E, Cerami A, Henderson G B (1991) An iron carboxylate bond links the heme units of malaria pigment. Proc Nat Acad Sci USA 88: 325–9.
27. Slater A F G, Cerami A (1992) Inhibition by chloroquine of a novel haem polymerase enzyme activity in malaria trophozoites. Nature 355: 167–9.
28. Kwiatkowski D, Hill A V S, Sambou I, Twumasi P, Castracane J, Manogue K R, Cerami A, Brewster D R, Greenwood B M. Tumor necrosis factor concentration in fatal cerebral, non-fatal cerebral, and uncomplicated *Plasmodium falciparum* malaria. (1990) *Lancet*:336, 1201–1204.
29. Lau P T S, Gompf T E. Reaction of quinones with thiourea. A novel route to 2-amino-6-hydroxybenzothiazoles and 2-amino-5-hydroxynaphtho [1,2-d]thiazoles. (1970) *J. Org. Chem*:35, 4103–4108.
30. Schwarzer E, Turrini F, Ulliers D, Giribaldi G, Ginsburg H, Arese P. Impairment of macrophage functions after ingestion of *Plasmodium falciparum*-infected erythrocytes or isolated malarial pigment. (1992) *J. Exp. Med*: 176, 1033–1041.
31. Turrini F, Schwarzer E, Arese P. The involvement of hemozoin toxicity in depression of cellular immunity. (1993) *Parasitology Today*:9(8), 297–300.

What is claimed is:

1. A method for depolymerizing hemozoin in a mammal infected with malaria comprising administering to said mammal a hemozoin-depolymerizing effective amount of a compound of the formula

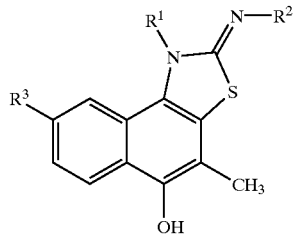

wherein $R^1$ is hydrogen, alkenyl, hydroxy(lower)alkyl, di[(lower)alkyl]amino(lower)alkyl, a heterocyclic group or a lower alkyl group optionally substituted by a heterocyclic group; $R^2$ is cycloalkyl, alkenyl, lower alkyl, hydroxy(lower alkyl), di[hydroxy(lower)alkyl]amino(lower)alkyl, a heterocyclic group, or an aryl group optionally substituted by a 1-(guanylhydrazono)alkyl group; $R^3$ is hydrogen or a 1-(guanylhydrazono)alkyl group; or a pharmaceutically acceptable salt therefor.

2. The method of claim 1 wherein $R^1$ is selected from the group consisting of hydroxyethyl, allyl, dimethylaminopropyl, morpholinopropyl, methylpiperazinoethyl, and ethyl.

3. The method of claim 1 wherein $R^2$ is selected from the group consisting of cyclohexyl, allyl, phenyl, di(hydroxyethyl)aminoethyl, ethyl, propyl, hydroxyethyl, and 3-[1-(guanylhydrazono)ethyl]phenyl.

4. The method of claim 1 wherein said compound is
1-ethyl-2-(ethylimino)-1,2-dihydro-4-methylnaphtho[1,2-d]-thiazol-5-ol;
1,2-dihydro-1,4-dimethyl-2-[[3-(4-methyl-1-piperazinyl)propyl]imino]naphtho[1,2-d]-thiazol-5-ol;
2-(cyclohexylimino)-1,2-dihydro-4-methyl-1-[3-(dimethylamino)propyl]naphtho[1,2-d]thiazol-5-ol;
2-[[3-[1-[2-(aminoiminomethyl)hydrazono]ethyl]phenyl]amino]-4-methylnaphtho[1,2-d]thiazol-5-ol;
2-[[3-[bis(2-hydroxyethyl)amino]propyl]imino]-1,2-dihydro-1,4-dimethylnaphtho[1,2-d]thiazol-5-ol;
1,2-dihydro-4-methyl-1-(2-propenyl)-2-(2-propenylimino)naphtho[1,2-d]thiazol-5-ol;
4-methyl-2-(2-propenylamino)naphtho[1,2-d]thiazol-5-ol;
2-(cyclohexylimino)-5-hydroxy-4-methylnaphtho[1,2-d]thiazole-1(2H)-ethanol;
1,2-dihydro-2-[(2-hydroxyethyl)imino]-1,4-dimethylnaphtho[1,2-d]thiazol-5-ol;
1,2-dihydro-1,4-dimethyl-2-(phenylimino)naphtho[1,2-d]thiazol-5-ol;
1,2-dihydro-4-methyl-2-(phenylimino)naphtho[1,2-d]thiazol-5-ol;
4-methyl-2-[[3-(4-morpholino)propyl]amino]naphtho[1,2-d]thiazol-5-ol;
8-[1-[2-(aminoiminomethyl)hydrazono]ethyl]-2-(butylimino)-1,2-dihydro-1,4-dimethylnaphtho[1,2-d]thiazol-5-ol;
2-(cyclohexylimino)-1,2-dihydro-4-methyl-1-[3-(4-morpholino)propyl]naphtho[1,2-d]thiazol-5-ol;
2-(cyclohexylimino)-1,2-dihydro-4-methyl-1-[3-(4-methyl-l1-piperazinyl)propyl]naphtho[1,2-d]thiazol-5-ol;
2-[[3-(dimethylamino)propyl]imino]-1,2-dihydro-1,4-dimethylnaphtho[1,2-d]thiazol-5-ol; or
1,2-dihydro-4-methyl-1-[3-(dimethylamino)propyl]-2-(1-methylethyl)aminonaphtho[1,2-d]thiazol-5-ol.

5. The method of claim 1, wherein said administration comprises pulmonary, nasal or injection delivery.

6. The method of claim 1, wherein said injection delivery comprises intravenous, intra-arterial, intramuscular or intra cranial administration.

7. The method of claim 1, wherein said hemozion-depolymerizing effective amount of the compound comprises a dose of about 1 mg to 500 mg.

8. The method of claim 1, wherein said hemozoin-depolymerizing effective amount of said compound comprises a dose of about 50 mg to 300 mg.

* * * * *